US012673990B2

(12) United States Patent
Bailey et al.

(10) Patent No.:  US 12,673,990 B2
(45) Date of Patent:       Jul. 7, 2026

(54) CR2 BINDING PROTEINS AND THEIR USE IN MEDICAL THERAPY

(71) Applicant: GLAXOSMITHKLINE INTELLECTUAL PROPERTY DEVELOPMENT LIMITED, Brentford (GB)

(72) Inventors: James Matthew Bailey, Stevenage (GB); Gerben Bouma, Stevenage (GB); Michael Neil Burden, Stevenage (GB); Caroline J. Dimech, Stevenage (GB); David Dixon, Stevenage (GB); Gabriela Dos Santos Cruz De Mantos, Stevenage (GB); Christian Ellson, Stevenage (GB); Laura J. Hook, Stevenage (GB); Semra Kitchen, Stevenage (GB); Eleonora Lekova, Stevenage (GB); Emilie Madura, Stevenage (GB); Kiran Nistala, Stevenage (GB); Jian Zhang, Stevenage (GB)

(73) Assignee: GlaxoSmithKline Intellectual Property Development Limited (GB)

( * ) Notice: Subject to any disclaimer, the term of this patent is extended or adjusted under 35 U.S.C. 154(b) by 1136 days.

(21) Appl. No.: 17/639,096

(22) PCT Filed: Aug. 28, 2020

(86) PCT No.: PCT/EP2020/074049
§ 371 (c)(1),
(2) Date: Feb. 28, 2022

(87) PCT Pub. No.: WO2021/038023
PCT Pub. Date: Mar. 4, 2021

(65) Prior Publication Data
US 2023/0032643 A1       Feb. 2, 2023

(30) Foreign Application Priority Data
Aug. 30, 2019    (GB) .................................... 1912437

(51) Int. Cl.
*C07K 16/28*       (2006.01)
*A61K 39/395*      (2006.01)
*A61P 31/18*       (2006.01)
*A61P 37/00*       (2006.01)

(52) U.S. Cl.
CPC .............. *C07K 16/28* (2013.01); *A61P 31/18* (2018.01); *A61P 37/00* (2018.01); *C07K 2317/52* (2013.01); *C07K 2317/565* (2013.01); *C07K 2317/732* (2013.01)

(58) Field of Classification Search
None
See application file for complete search history.

(56) References Cited

FOREIGN PATENT DOCUMENTS

WO        2002092011 A2    11/2002

OTHER PUBLICATIONS

Guthridge et al. Epitope Mapping Using the X-Ray Crystallographic Structure of Complement Receptor Type 2 (CR2)/CD21: Identification of a Highly Inhibitory Monoclonal Antibody That Directly Recognizes the CR2-C3d Interface1. The Journal of Immunology, vol. 167: 5758-5766.; (2001). (Year: 2001).*

Yu et al. A methodological review of induced animal models of autoimmune diseases. Autoimmunity Reviews 17:473-479 ( 2018). (Year: 2018).*

Lommatzsch et al. Roads to remission: evolving treatment concepts in type 2 inflammatory diseases. The Lancet vol. 80:1-13, (Feb. 2025). (Year: 2025).*

Justice et al. Using the mouse to model human disease: increasing validity and reproducibility, Disease, Models & Mechanisms 9:101-103, (2016). (Year: 2016).*

Al Qaraghuli et al. Antibody-protein binding and conformational changes: identifying allosteric signalling pathways to engineer a better effector response. Nature Scientific Reports 10:13969, 2020). (Year: 2020).*

Edwards et al. The remarkable flexibility of the human antibody repertoire; isolation of over one thousand different antibodies to a single protein, BLyS. Journal of Molecular Biology 334:103-118; (2003). (Year: 2003).*

Lloyd et al. Modelling the human immune response: performance of a 10(11) human antibody repertoire against a broad panel of therapeutically relevant antigens. Protein Engineering, Eng. Design & Selection 22(3): 159-168; (2009). (Year: 2009).*

Goel et al. Plasticity within the antigen-combining site may manifest as molecular mimicry in the humoral immune response. J. Immunol. 173: 7358-7367; (2004). (Year: 2004).*

Poosarla et al. Computational De Novo Design of Antibodies Binding to a Peptide With High Affinity. Biotechn. Bioeng. 114(6): 1331-1342; (2017). (Year: 2017).*

Guthridge J. M. et al: "Epitope mapping using the X-ray crystallographic structure of complement receptor type 2 (CR2)/CD21: identification of a highly inhibitory monoclonal antibody that directly recognizes the CR2-C3d interface", The Journal of Immunology, American Assoc i a ti on of Immunologists, US, vol. 167, No. 10, Nov. 15, 2001 (Nov. 15, 2001), pp. 5758-5766, XP002318006, ISSN: 0022-1767.

Joel M. Guthridge et al., Epitope Mapping Using the X-Ray Crystallographic Structure of Complement Receptor Type 2 (CR2)/CD21: Identification of a Highly Inhibitory Monoclonal Antibody That Directly Recognizes the CR2-C3d Interface, J Immunol., 2001, vol. 167, issue 10, pp. 5758-5766.

Laco Kacani et al., Detachment of Human Immunodeficiency Virus Type 1 from Germinal Centers by Blocking Complement Receptor Type 2, Journal of Virology, 2000, vol. 74, No. 17, pp. 7997-8002.

* cited by examiner

*Primary Examiner* — Bridget E Bunner
*Assistant Examiner* — Regina M DeBerry
(74) *Attorney, Agent, or Firm* — J. Scott Young

(57)              ABSTRACT

The present invention provides CR2 binding proteins which bind to human CR2, pharmaceutical compositions comprising said CR2 binding proteins and their use in the treatment or prevention of autoimmune and/or inflammatory conditions, infectious diseases and malignancies associated with the Epstein-Barr virus (EBV); and their use as vaccine adjuvants/antigen carriers.

8 Claims, 9 Drawing Sheets

Figure 1:
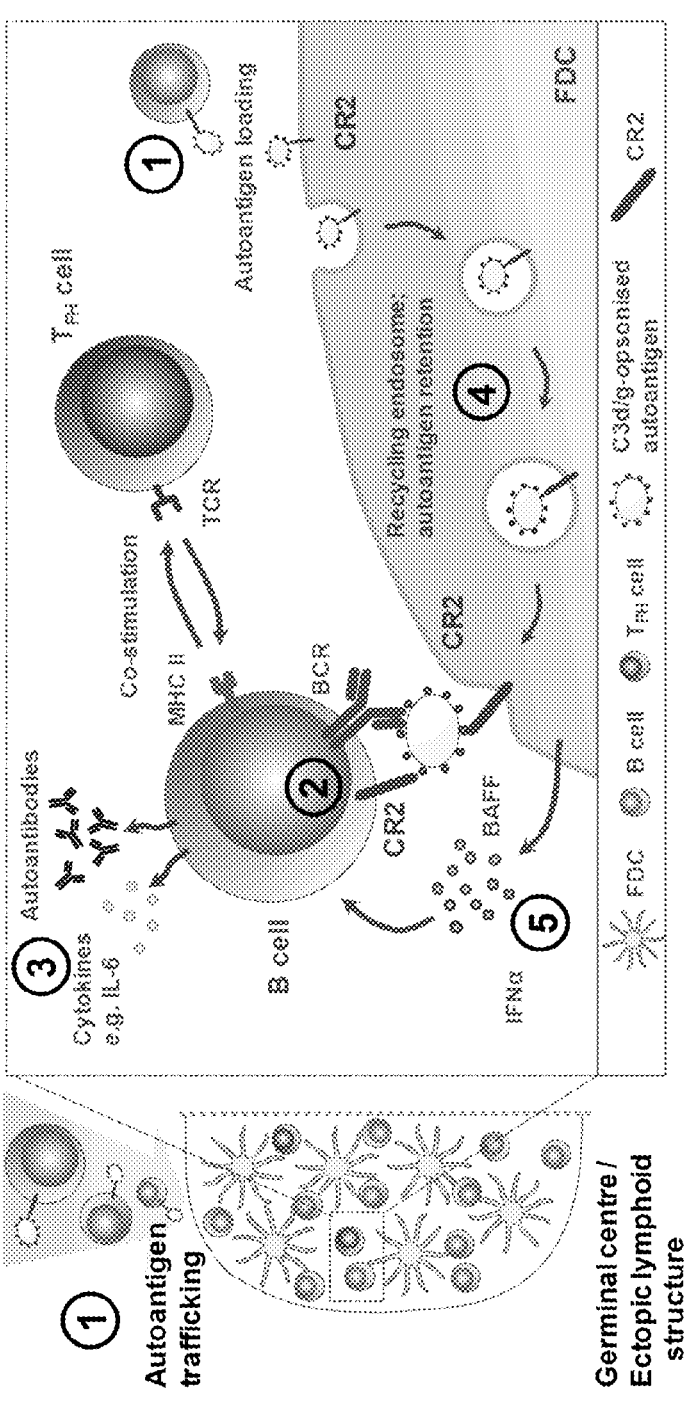

Specification includes a Sequence Listing.

a.

b.

CR2 BINDING PROTEINS AND THEIR USE IN MEDICAL THERAPY

CROSS REFERENCE TO RELATED APPLICATIONS

The instant application claims priority to Great Britain Provisional Patent Application No. 1912437.9 filed Aug. 30, 2019 and PCT/2020/074049 filed Aug. 28, 2020. The contents of these applications are incorporated by reference herein in their entirety.

FIELD OF THE DISCLOSURE

The present invention relates to CR2 binding proteins, that bind to and neutralise complement receptor 2 (CR2 or CD21). The invention also concerns methods of treating diseases or disorders with said CR2 binding proteins and pharmaceutical compositions comprising CR2 binding proteins. Other aspects of the present invention will be apparent from the description below.

BACKGROUND TO THE DISCLOSURE

The complement system is a set of evolutionarily-conserved plasma proteins that are part of the innate immune response to invading pathogens. Proteolytic activation of complement occurs on activating surfaces resulting in the deposition of active complement components with a range of effector functions, including modulation of the adaptive immune response. Complement receptor 2 (CR2), also known as CD21, is a membrane bound glycoprotein of 145 kDa predominantly expressed on B lymphocytes and follicular dendritic cells (FDCs), acting as a bridge between innate and adaptive immunity. CR2 is the receptor for the smallest covalently bound complement component 3 (C3) fragments, C3dg and C3d (together referred to as C3d/g) and has weaker binding to iC3b. Interferon alpha, double-stranded DNA and Epstein-Barr virus gp350/220 have also been described as ligands for CR2.

CR2 plays three pivotal roles in adaptive immune responses by: 1) binding opsonised antigens and transporting them to and retaining them in lymphoid tissue, 2) reducing the threshold of B cell activation and 3) driving affinity maturation and germinal centre formation through B cell-FDC cross talk. The importance of these mechanisms in man is confirmed by rare cases of CR2 deficiency; patients have significantly fewer memory B cells and have reduced antibody diversity and serum immunoglobulin levels.

Germinal centres (GCs) and, in the context of autoimmunity, ectopic lymphoid structures (ELS) that form outside the primary and secondary lymphoid organs, are pivotal to the autoimmune response. The role of CR2 in GC and ELS formation, maintenance and productivity are several-fold (see FIG. 1):

1) carriage of C3d/g-opsonised antigens on non-cognate B cells in the circulation and within GCs and ELSs;
2) lowering the threshold of B cell activation by C3d/g-opsonised antigens within the GC/ELS;
3) stimulation of B cell outputs downstream of CR2/BCR co-ligation e.g. antibody production;
4) retention of C3d/g-opsonised antigens within an FDC reservoir for presentation to B cells; and
5) activation of FDC function e.g. cytokine production.

Disruption of these CR2-dependent mechanisms is predicted to have a major impact on GC/ELS, including reduction of antigen availability, disruption of FDC: B cell interactions, reduction of antigen-specific antibodies, and disruption of T follicular helper (Tfh) cell crosstalk with B cells.

Many autoimmune and/or inflammatory conditions are characterised by high levels of autoantibodies, suggestive of failure of immune tolerance and dysregulation of B cell activation. For autoimmune diseases such as Sjögren's syndrome, systemic lupus erythematosus (SLE) or rheumatoid arthritis (RA), blocking the complement C3d/g-CR2 interaction with a CR2-blocking molecule will increase the activation threshold on B cells and prevent activation and expansion of autoantibody producing B cells in response to self-antigen.

Viral diseases, for example HIV, can be difficult to treat due to the persistence of long-lived viral reservoirs in FDCs and lymphatic tissue. Antigen binding, retention in excess of one year, and presentation are largely dependent on the CR2-dependent capture of C3 fragment-coated antigens Once C3d/g-opsonised antigen has been transferred to the FDC from marginal zone (MZ) B cells, the intact antigen is rapidly internalized by means of small non-degradative endosomal vesicles. These vesicles are then periodically re-cycled to the cell surface where intact antigen and other FDC surface proteins can be recognized and acquired by cognate B cells. Similarly, C3d/g-opsonised HIV virions are captured and retained long-term in these non-degradative endosomes, representing a long-lived viral reservoir.

Molecules that bind to CR2 could be used as adjuvants/antigen carriers to amplify immune responses to immunisation. Low doses of antigen coupled to anti-CR2 antibodies has been found to induce rapid and enduring IgG immune responses in mice and cynomolgus monkeys (Whipple, E. C. et al., Mol. Immunol., 2007. 44 (4): p. 377-388). In summary, there remains a need for treatment of autoimmune and/or inflammatory conditions, infectious diseases and other disorders or conditions in which B cell activation or retention of C3d or C3dg opsonised antigens within an FDC reservoir is implicated. Further there remains a need for alternative vaccine adjuvants and antigen carriers.

SUMMARY OF THE DISCLOSURE

The present invention provides CR2 binding proteins which bind to novel epitopes of CR2 and prevent ligand binding to the CR2 receptor, hereinafter referred to as "CR2 binding proteins".

The present invention also provides a CR2 binding protein, wherein said CR2 binding protein binds to one or more residues within the linker between the two short complement repeat domains and/or near the C-terminus of human CR2. In one embodiment the CR2 binding protein binds to human CR2 at one or more amino acid residues within SEQ ID NO:2 and/or SEQ ID NO:71. In another embodiment the CR2 binding protein binds to human CR2 at one or more amino acid residues within SEQ ID NO:2. In another embodiment the CR2 binding protein binds to human CR2 at one or more amino acid residues within SEQ ID NO:71. In another embodiment the CR2 binding protein protects residues 66 to 70 (SEQ ID NO:2) of CR2 from deuterium exchange in HDX-MS analysis. In a further embodiment the CR2 binding protein protects residues 66 to 70 (SEQ ID NO:2) and/or residues 104-127 (SEQ ID NO:71) of CR2 from deuterium exchange in HDX-MS analysis.

The present invention also provides a CR2 binding protein wherein said CR2 binding protein is an antibody. In one embodiment the antibody is a monoclonal antibody. In another embodiment the monoclonal antibody is an IgG1 or IgG4. In another embodiment the monoclonal antibody is an IgG1. In another embodiment, the antibody comprises in its light chain variable region a CDR1 comprising the amino acid sequence set out in SEQ ID NO:10, a CDR2 comprising the amino acid sequence set out in SEQ ID NO: 11 and a CDR3 comprising the amino acid sequence set out in SEQ ID NO: 12. In another embodiment, the antibody comprises in its heavy chain variable region a CDR1 comprising the amino acid sequence set out in SEQ ID NO:7, a CDR2 comprising the amino acid sequence set out in SEQ ID NO:8 and a CDR3 comprising the amino acid sequence set out in SEQ ID NO: 9. In another embodiment, the antibody comprises a variable light chain amino acid sequence as set out in SEQ ID NO:6. In another embodiment, the antibody comprises a variable heavy chain amino acid sequence as set out in SEQ ID NO:5. In another embodiment, the antibody comprises a light chain amino acid sequence as set out in SEQ ID NO:4. In another embodiment, the antibody comprises a heavy chain amino acid sequence as set out in SEQ ID NO:3. In a further embodiment, the antibody comprises a light chain amino acid sequence as set out in SEQ ID NO:4. and a heavy chain amino acid sequence as set out in SEQ ID NO:3.

The present invention also provides a CR2 binding protein comprising a constant region such that the CR2 binding protein has reduced ADCC and/or complement activation or effector functionality. In one embodiment the CR2 binding protein constant region comprises substitutions at positions 235 and 237 (EU index numbering) with alanine residues. In another embodiment the CR2 binding protein constant region comprises substitutions at positions 234 and 235 (EU index numbering) with alanine residues.

The present invention also provides a CR2 binding protein which is human, humanised or chimeric. In one embodiment the CR2 binding protein is human.

The present invention also provides a CR2 binding protein comprising any one or a combination of the following CDRs: CDRH1, CDRH2, CDRH3 from SEQ ID NO:5 and/or CDRL1, CDRL2, CDRL3 from SEQ ID NO:6. In one embodiment the CR2 binding protein comprises in its light chain variable region a CDR1 comprising the amino acid sequence set out in SEQ ID NO:10, a CDR2 comprising the amino acid sequence set out in SEQ ID NO:11 and a CDR3 comprising the amino acid sequence set out in SEQ ID NO:12, or a variant of one or all of these CDRs, wherein the CDR variant has 1, 2 or 3 amino acid modifications. In another embodiment the CR2 binding protein comprises in its light chain variable region a CDR1 comprising the amino acid sequence set out in SEQ ID NO:10, a CDR2 comprising the amino acid sequence set out in SEQ ID NO:11 and a CDR3 comprising the amino acid sequence set out in SEQ ID NO:12. In another embodiment the CR2 binding protein comprises in its heavy chain variable region a CDR1 comprising the amino acid sequence set out in SEQ ID NO:7, a CDR2 comprising the amino acid sequence set out in SEQ ID NO:8 and a CDR3 comprising the amino acid sequence set out in SEQ ID NO:9, or a variant of one or all of these CDRs, wherein the CDR variant has 1, 2 or 3 amino acid modifications. In another embodiment the CR2 binding protein comprises in its heavy chain variable region a CDR1 comprising the amino acid sequence set out in SEQ ID NO:7, a CDR2 comprising the amino acid sequence set out in SEQ ID NO:8 and a CDR3 comprising the amino acid sequence set out in SEQ ID NO:9. In another embodiment the CR2 binding protein comprises a variable light chain amino acid sequence as set out in SEQ ID NO:6. In another embodiment the CR2 binding protein comprises a variable heavy chain amino acid sequence as set out in SEQ ID NO:5. In another embodiment the CR2 binding protein comprises a variable light chain amino acid sequence as set out in SEQ ID NO:6 and a variable heavy chain amino acid sequence as set out in SEQ ID NO:5. In another embodiment the CR2 binding protein comprises a light chain amino acid sequence as set out in SEQ ID NO:4. In another embodiment the CR2 binding protein comprises a heavy chain amino acid sequence as set out in SEQ ID NO:3. In a further embodiment the CR2 binding protein comprises a light chain amino acid sequence as set out in SEQ ID NO:4 and a heavy chain amino acid sequence as set out in SEQ ID NO:3.

The present invention also provides a CR2 binding protein comprising any one or a combination of the following CDRs: CDRH1, CDRH2, CDRH3 from SEQ ID NO:17 and/or CDRL1, CDRL2, CDRL3 from SEQ ID NO: 18. In one embodiment the CR2 binding protein comprises in its light chain variable region a CDR1 comprising the amino acid sequence set out in SEQ ID NO:22, a CDR2 comprising the amino acid sequence set out in SEQ ID NO:23 and a CDR3 comprising the amino acid sequence set out in SEQ ID NO:24, or a variant of one or all of these CDRs, wherein the CDR variant has 1, 2 or 3 amino acid modifications. In another embodiment the CR2 binding protein comprises in its light chain variable region a CDR1 comprising the amino acid sequence set out in SEQ ID NO:22, a CDR2 comprising the amino acid sequence set out in SEQ ID NO:23 and a CDR3 comprising the amino acid sequence set out in SEQ ID NO:24. In another embodiment the CR2 binding protein comprises in its heavy chain variable region a CDR1 comprising the amino acid sequence set out in SEQ ID NO: 19, a CDR2 comprising the amino acid sequence set out in SEQ ID NO:20 and a CDR3 comprising the amino acid sequence set out in SEQ ID NO:21, or a variant of one or all of these CDRs, wherein the CDR variant has 1, 2 or 3 amino acid modifications. In another embodiment the CR2 binding protein comprises in its heavy chain variable region a CDR1 comprising the amino acid sequence set out in SEQ ID NO:19, a CDR2 comprising the amino acid sequence set out in SEQ ID NO:20 and a CDR3 comprising the amino acid sequence set out in SEQ ID NO:21. In another embodiment the CR2 binding protein comprises a variable light chain amino acid sequence as set out in SEQ ID NO:18. In another embodiment the CR2 binding protein comprises a variable heavy chain amino acid sequence as set out in SEQ ID NO: 17. In another embodiment the CR2 binding protein comprises a variable light chain amino acid sequence as set out in SEQ ID NO:18 and a variable heavy chain amino acid sequence as set out in SEQ ID NO:17. In another embodiment the CR2 binding protein comprises a light chain amino acid sequence as set out in SEQ ID NO: 16. In another embodiment the CR2 binding protein comprises a heavy chain amino acid sequence as set out in SEQ ID NO:15. In a further embodiment the CR2 binding protein comprises a light chain amino acid sequence as set out in SEQ ID NO: 16 and a heavy chain amino acid sequence as set out in SEQ ID NO: 15.

The present invention also provides a CR2 binding protein comprising any one or a combination of the following CDRs: CDRH1, CDRH2, CDRH3 from SEQ ID NO:29 and/or CDRL1, CDRL2, CDRL3 from SEQ ID NO:30. In one embodiment the CR2 binding protein comprises in its light chain variable region a CDR1 comprising the amino acid sequence set out in SEQ ID NO:34, a CDR2 comprising the amino acid sequence set out in SEQ ID NO:35 and a CDR3 comprising the amino acid sequence set out in SEQ ID NO:36, or a variant of one or all of these CDRs, wherein the CDR variant has 1, 2 or 3 amino acid modifications. In another embodiment the CR2 binding protein comprises in its light chain variable region a CDR1 comprising the amino acid sequence set out in SEQ ID NO:34, a CDR2 comprising the amino acid sequence set out in SEQ ID NO:35 and a CDR3 comprising the amino acid sequence set out in SEQ ID NO:36. In another embodiment the CR2 binding protein comprises in its heavy chain variable region a CDR1 comprising the amino acid sequence set out in SEQ ID NO:31, a CDR2 comprising the amino acid sequence set out in SEQ ID NO:32 and a CDR3 comprising the amino acid sequence set out in SEQ ID NO:33, or a variant of one or all of these CDRs, wherein the CDR variant has 1, 2 or 3 amino acid modifications. In another embodiment the CR2 binding protein comprises in its heavy chain variable region a CDR1 comprising the amino acid sequence set out in SEQ ID NO:31, a CDR2 comprising the amino acid sequence set out in SEQ ID NO:32 and a CDR3 comprising the amino acid sequence set out in SEQ ID NO:33. In another embodiment the CR2 binding protein comprises a variable light chain amino acid sequence as set out in SEQ ID NO:30. In another embodiment the CR2 binding protein comprises a variable heavy chain amino acid sequence as set out in SEQ ID NO:29. In another embodiment the CR2 binding protein comprises a variable light chain amino acid sequence as set out in SEQ ID NO:30 and a variable heavy chain amino acid sequence as set out in SEQ ID NO:29. In another embodiment the CR2 binding protein comprises a light chain amino acid sequence as set out in SEQ ID NO:28. In another embodiment the CR2 binding protein comprises a heavy chain amino acid sequence as set out in SEQ ID NO:27. In a further embodiment the CR2 binding protein comprises a light chain amino acid sequence as set out in SEQ ID NO:28 and a heavy chain amino acid sequence as set out in SEQ ID NO:27.

The present invention also provides a CR2 binding protein wherein the equilibrium dissociation constant (KD) of the antigen binding protein-CR2 interaction is between 0.1 and 1 nM.

The present invention also provides a CR2 binding protein that competes for binding to CR2 with any one of the CR2 binding proteins.

The present invention also provides a nucleic acid molecule encoding any one of the CR2 binding proteins. In one embodiment the nucleic acid molecule sequence comprises SEQ ID NO: 13 encoding the heavy chain and/or SEQ ID NO: 14 encoding the light chain. In another embodiment the nucleic acid molecule sequence comprises SEQ ID NO:25 encoding the heavy chain and/or SEQ ID NO: 26 encoding the light chain. In a further embodiment the nucleic acid molecule sequence comprises SEQ ID NO:37 encoding the heavy chain and/or SEQ ID NO:38 encoding the light chain.

The present invention also provides an expression vector comprising a nucleic acid molecule encoding any one of the CR2 binding proteins. In one embodiment the expression vector comprises a nucleic acid molecule sequence comprising SEQ ID NO:13 encoding the heavy chain and/or SEQ ID NO: 14 encoding the light chain. In another embodiment the expression vector comprises a nucleic acid molecule sequence comprising SEQ ID NO:25 encoding the heavy chain and/or SEQ ID NO:26 encoding the light chain. In a further embodiment the expression vector comprises a nucleic acid molecule sequence comprising SEQ ID NO:37 encoding the heavy chain and/or SEQ ID NO:38 encoding the light chain.

The present invention also provides a recombinant host cell comprising an expression vector comprising a nucleic acid molecule encoding any one of the CR2 binding proteins.

The present invention also provides a CR2 binding protein expressed by a recombinant host cell comprising an expression vector comprising a nucleic acid molecule encoding any one of the CR2 binding proteins.

The present invention also provides a method for the production of a CR2 binding protein, comprising the step of culturing a recombinant host cell in a medium to produce the CR2 binding protein, and isolating or purifying the CR2 binding protein.

The present invention also provides a pharmaceutical composition comprising a CR2 binding protein and a pharmaceutically acceptable carrier or excipient.

The present invention also provides a CR2 binding protein that blocks interaction with C3d/g-coated complexes. In one embodiment, the invention provides a CR2 binding protein that blocks signalling, activation and antibody production downstream of BCR:CR2 co-ligation and also prevents C3d/g antigen binding to FDCs.

The present invention also provides a CR2 binding protein for use in therapy.

The present invention also provides a method for the treatment of an autoimmune and/or inflammatory condition in a subject in need thereof, comprising administering to said subject a therapeutically effective amount of a CR2 binding protein. In one embodiment there is provided a method for the treatment of Sjögren's syndrome in a subject in need thereof, comprising administering to said subject a therapeutically effective amount of a CR2 binding protein. In another embodiment there is provided a method for the treatment of rheumatoid arthritis in a subject in need thereof, comprising administering to said subject a therapeutically effective amount of a CR2 binding protein. In another embodiment there is provided a method for the treatment of systemic lupus erythematosus in a subject in need thereof, comprising administering to said subject a therapeutically effective amount of a CR2 binding protein. In another embodiment there is provided a method for the treatment of vasculitis in a subject in need thereof, comprising administering to said subject a therapeutically effective amount of a CR2 binding protein. In a further embodiment there is provided a method for the treatment of anti-neutrophil cytoplasmic antibody (ANCA)-associated vasculitis in a subject in need thereof, comprising administering to said subject a therapeutically effective amount of a CR2 binding protein.

The present invention also provides a method for the treatment of an infectious disease in a subject in need thereof, comprising administering to said subject a therapeutically effective amount of a CR2 binding protein. In one embodiment there is provided a method for the treatment of HIV in a subject in need thereof, comprising administering to said subject a therapeutically effective amount of a CR2 binding protein.

The present invention also provides a method for amplifying an immune response to an immunisation in a subject in need thereof, comprising administering to said subject a therapeutically effective amount of a CR2 binding protein.

The present invention also provides a method for the treatment of a malignancy associated with EBV in a subject in need thereof, comprising administering to said subject a therapeutically effective amount of a CR2 binding protein.

The present invention also provides the use of a CR2 binding protein in the manufacture of a medicament for the treatment of an autoimmune and/or inflammatory condition. In one embodiment there is provided the use of a CR2 binding protein in the manufacture of a medicament for the treatment of Sjögren's syndrome. In another embodiment there is provided the use of a CR2 binding protein in the manufacture of a medicament for the treatment of rheumatoid arthritis. In another embodiment there is provided the use of a CR2 binding protein in the manufacture of a medicament for the treatment of systemic lupus erythematosus. In another embodiment there is provided the use of a CR2 binding protein in the manufacture of a medicament for the treatment of vasculitis. In a further embodiment there is provided the use of a CR2 binding protein in the manufacture of a medicament for the treatment of anti-neutrophil cytoplasmic antibody (ANCA)-associated vasculitis.

The present invention also provides the use of a CR2 binding protein in the manufacture of a medicament for the treatment of an infectious disease. In one embodiment there is provided the use of a CR2 binding protein in the manufacture of a medicament for the treatment of HIV.

The present invention also provides the use of a CR2 binding protein in the manufacture of a vaccination for amplifying an immune response to an immunisation.

The present invention also provides the use of a CR2 binding protein in the manufacture of a medicament for the treatment of a malignancy associated with EBV.

The present invention also provides a CR2 binding protein for use in the treatment of an autoimmune and/or inflammatory condition. In one embodiment there is provided a CR2 binding protein for use in the treatment of Sjögren's syndrome. In another embodiment there is provided a CR2 binding protein for use in the treatment of rheumatoid arthritis. In another embodiment there is provided a CR2 binding protein for use in the treatment of systemic lupus erythematosus. In another embodiment there is provided a CR2 binding protein for use in the treatment of vasculitis. In a further embodiment there is provided a CR2 binding protein for use in the treatment of anti-neutrophil cytoplasmic antibody (ANCA)-associated vasculitis.

The present invention also provides a CR2 binding protein for use in the treatment of an infectious disease. In one embodiment there is provided a CR2 binding protein for use in the treatment of HIV.

The present invention also provides a CR2 binding protein for use in the treatment of a malignancy associated with EBV.

The present invention also provides a CR2 binding protein for use in amplifying an immune response to an immunisation.

Other aspects and embodiments of the invention will be apparent from the detailed description that follows.

DESCRIPTION OF DRAWINGS/FIGURES

FIG. 1 shows the roles of CR2 in GC/ELS formation and productivity. CR2-dependent processes are shown.

Figure 2A:
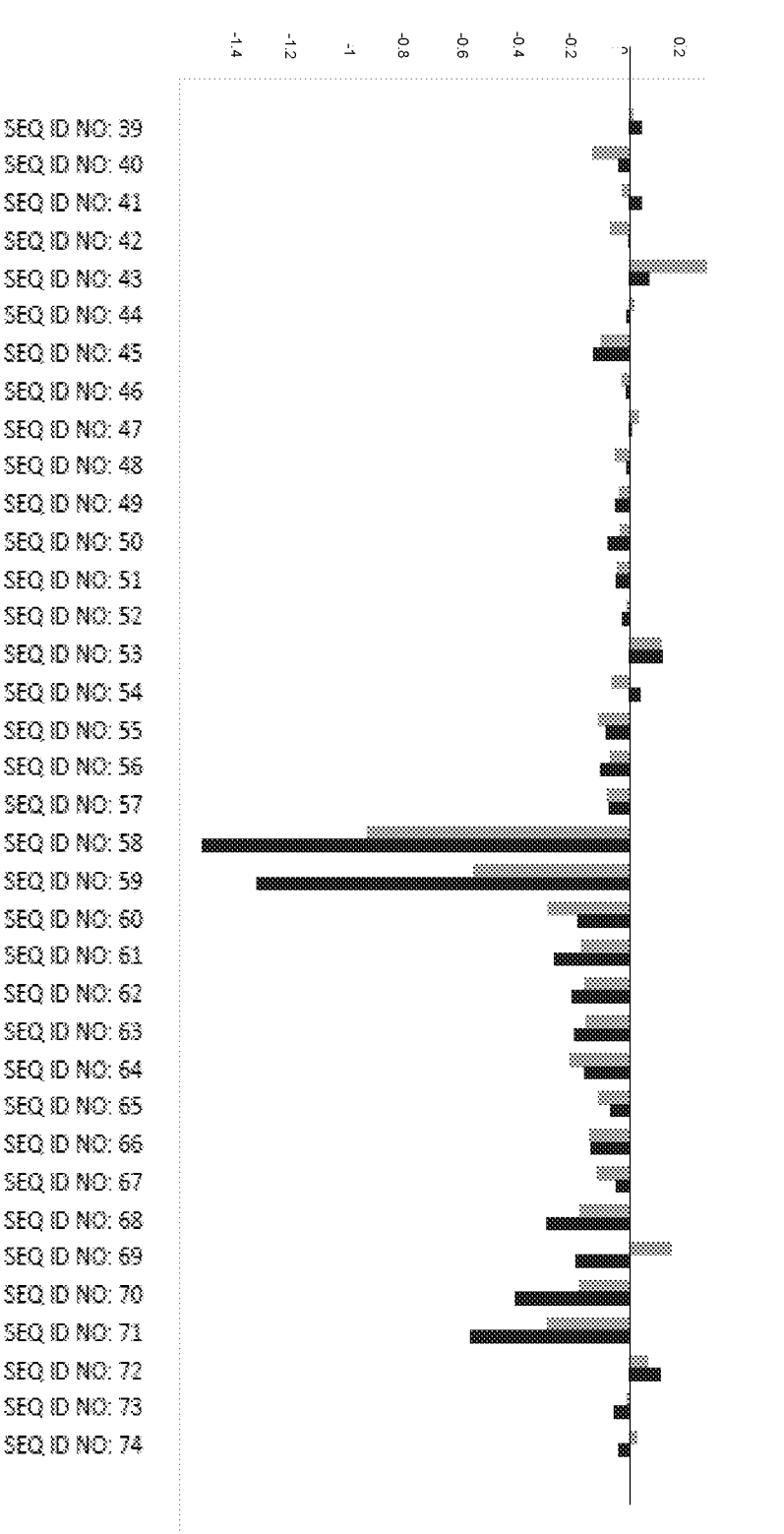
Figure 2B:
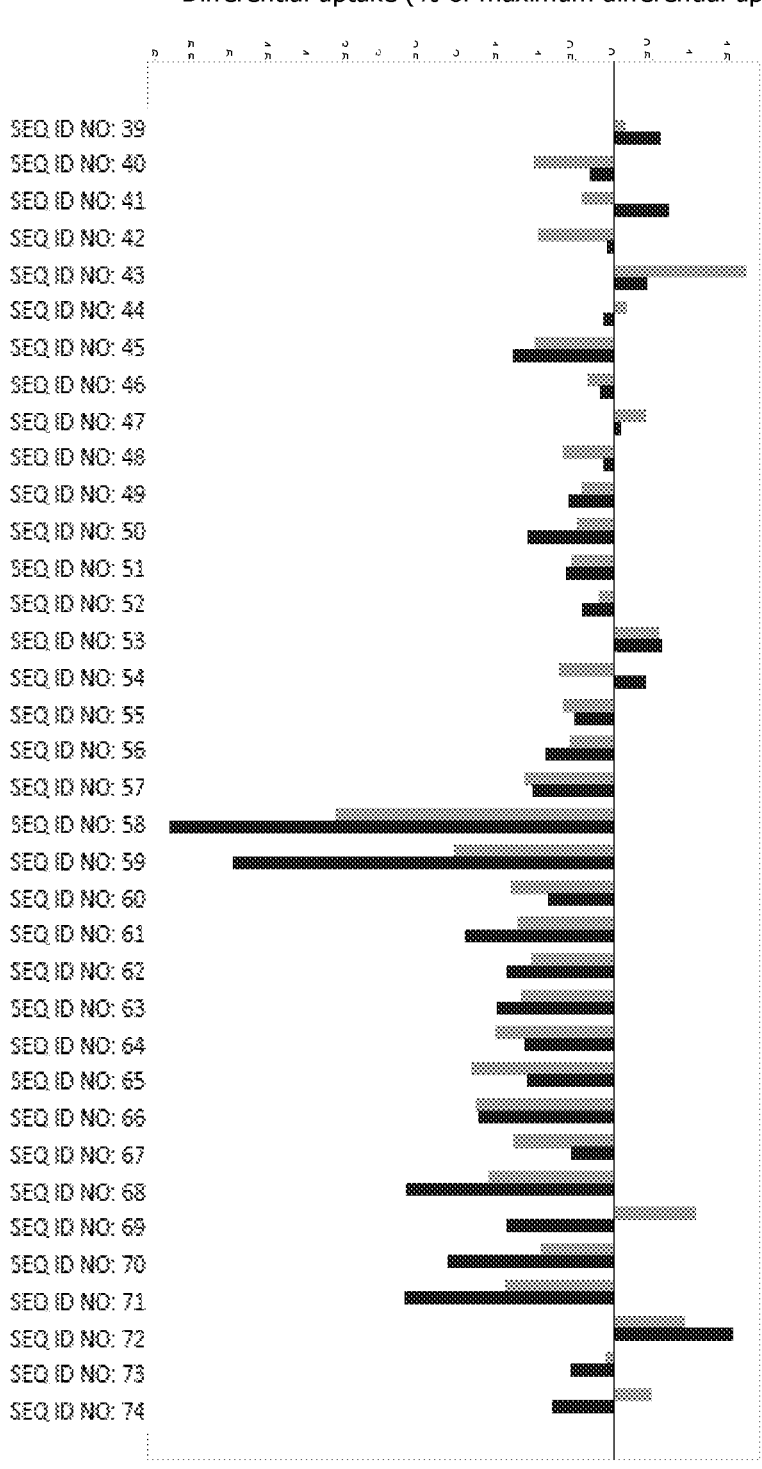

FIG. 2 shows HDX-MS derived differential deuteration of CR2 peptides between samples in the absence and presence of mAb 1053. FIG. 2A shows averaged differential uptake in Da per peptide; FIG. 2B shows average differential uptake normalised per peptide residue, as a percentage of a maximum differential deuteration of 1 Da per residue (assuming that a peptide with n non-proline residues has n−2 amides with measurable proton exchange). Each peptide is shown with its position in the CR2 construct used and its sequence. Bars are coloured by time of exposure to deuterated buffer (0.5 min=grey; 5 min=black).

Figure 3:
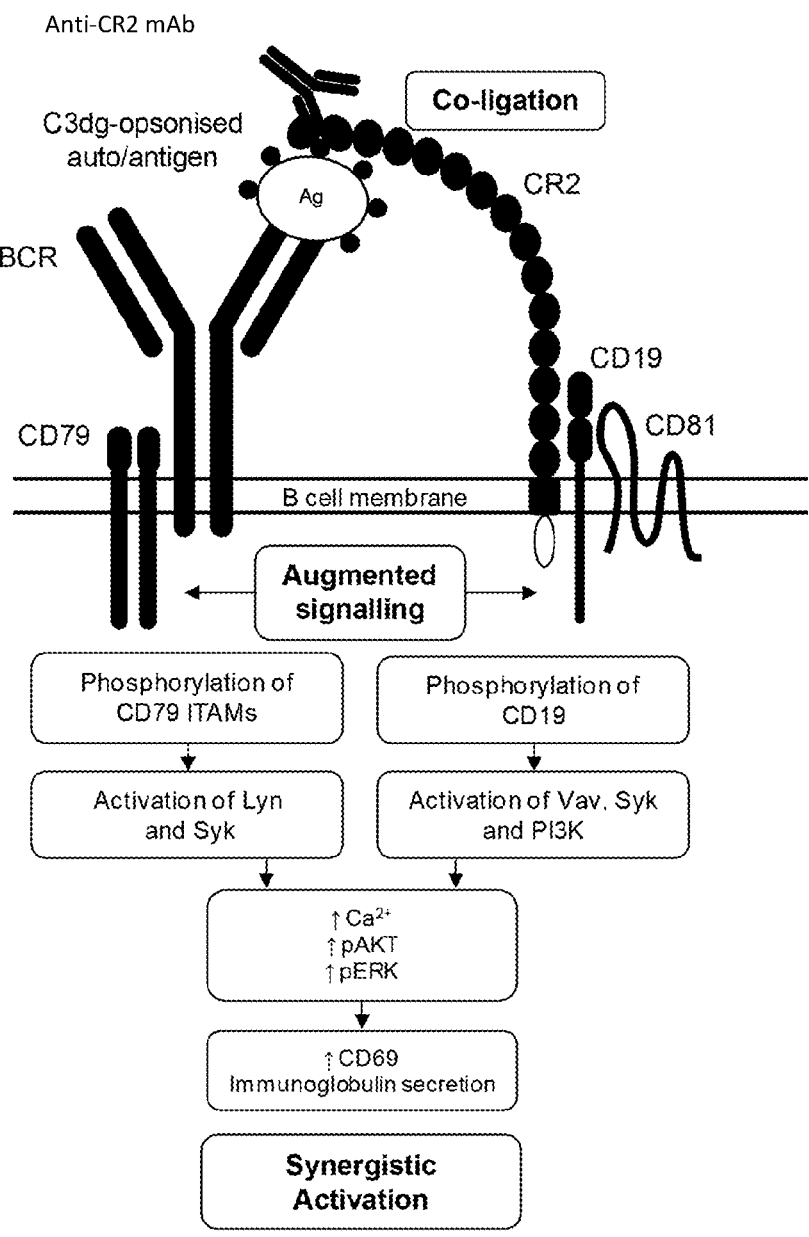

FIG. 3: illustrates the synergistic activation of B cells through co-ligation of the BCR and CR2 by C3dg-opsonised antigen. Antigen opsonised with the CR2 ligand C3d/g co-ligates the BCR and CR2. The BCR binds to its cognate antigen, and CR2 binds to C3d/g which is covalently bound to the antigen (Ag). Co-ligation of the BCR and CR2 leads to augmented signalling through both CD79 (in complex with the BCR) and CD19 (part of the B cell co-receptor complex), leading to downstream signalling and synergistic B cell activation (adapted from Carroll and Isenman, 2012, *Immunity*, 37 (2). 119-207).

Figure 4:
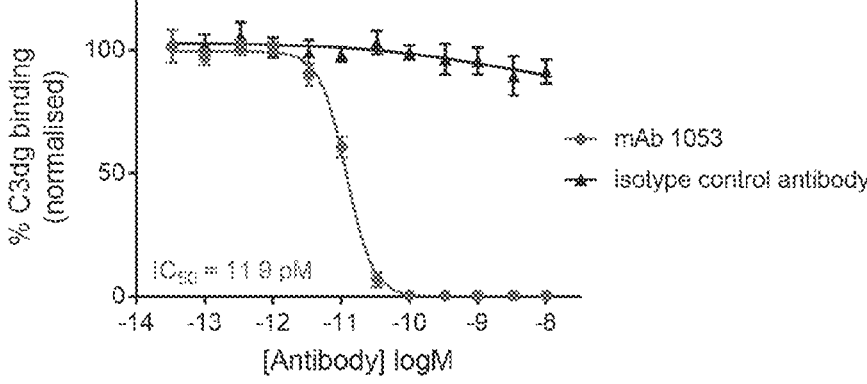

FIG. 4: demonstrates that pre-incubation with mAb 1053 prevents binding of model C3dg-opsonised ligand to primary human non-cognate B cells, in a dose-dependent manner.

Figure 5:
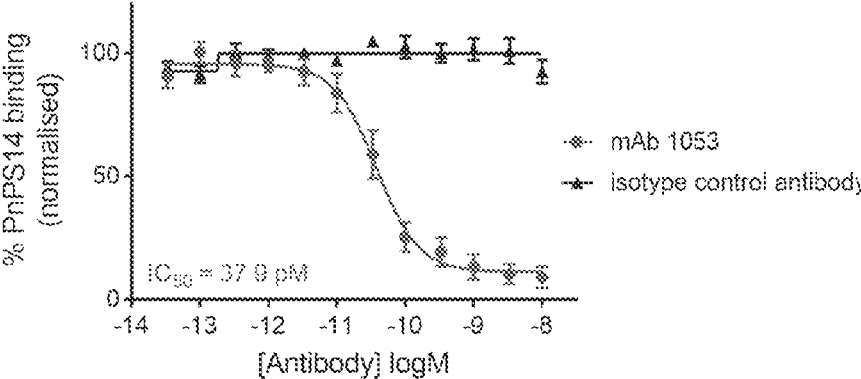

FIG. 5: demonstrates that pre-incubation with mAb 1053 prevents binding of serum-opsonised PnPS14 to primary human non-cognate B cells in a dose-dependent manner.

Figure 6:
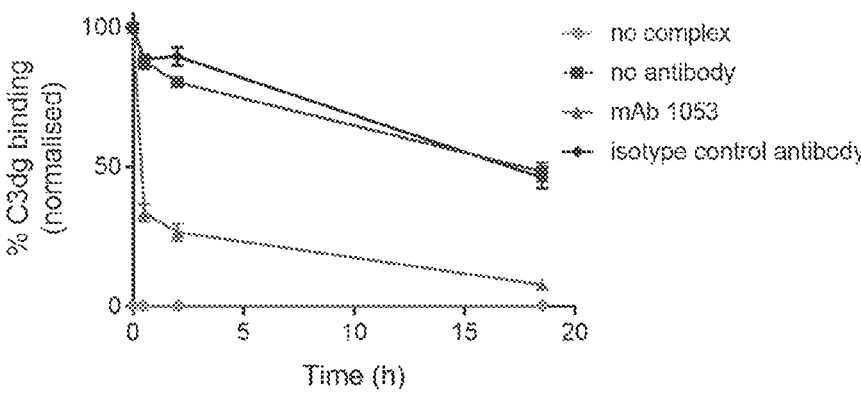

FIG. 6: demonstrates that mAb 1053 rapidly competes off pre-bound model C3dg-opsonised ligand from primary human non-cognate B cells.

Figure 7:
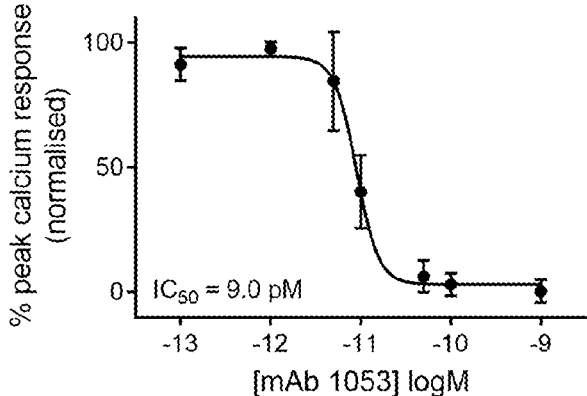

FIG. 7: demonstrates that mAb 1053 inhibits CR2-mediated intracellular calcium flux in primary human B cells in a dose-dependent manner.

Figure 8A:
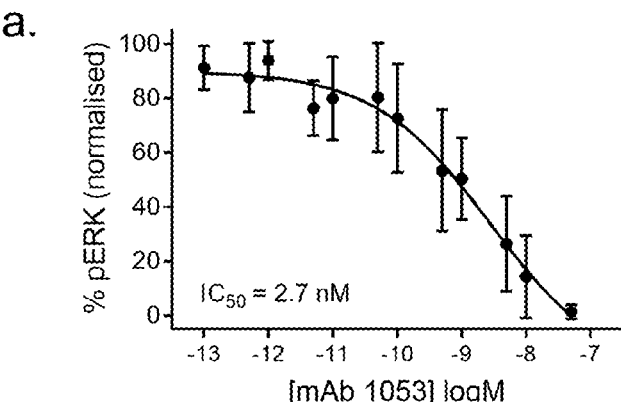
Figure 8B:
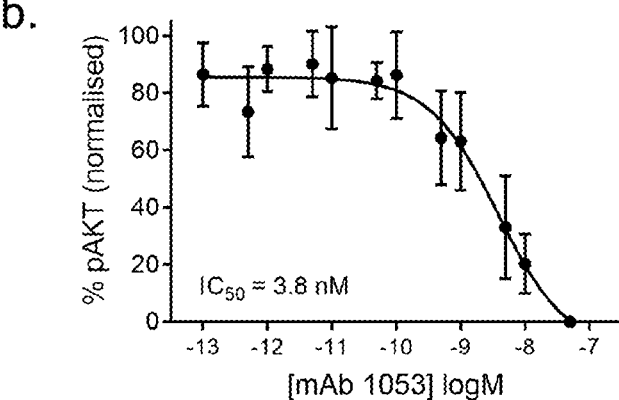

FIGS. 8a and 8b: demonstrate that mAb 1053 inhibits CR2-mediated phospho-protein signalling in primary human B cells in a dose-dependent manner.

Figure 9:
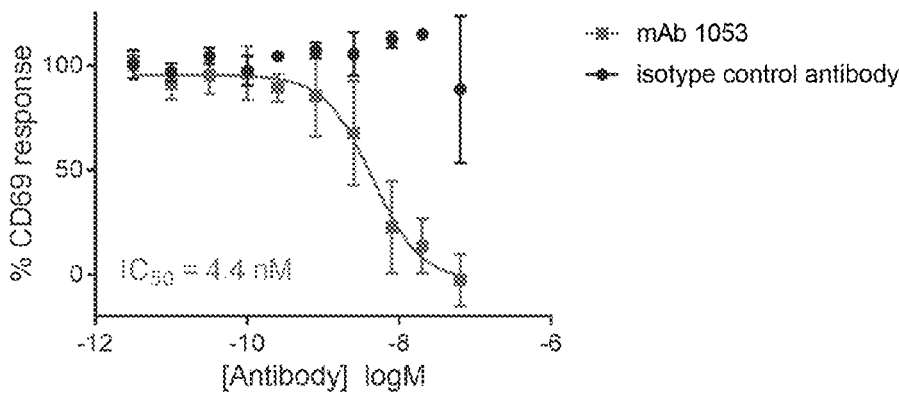

FIG. 9: demonstrates that mAb 1053 inhibits CR2-mediated CD69 upregulation in primary human B cells in a dose-dependent manner.

Figure 10:
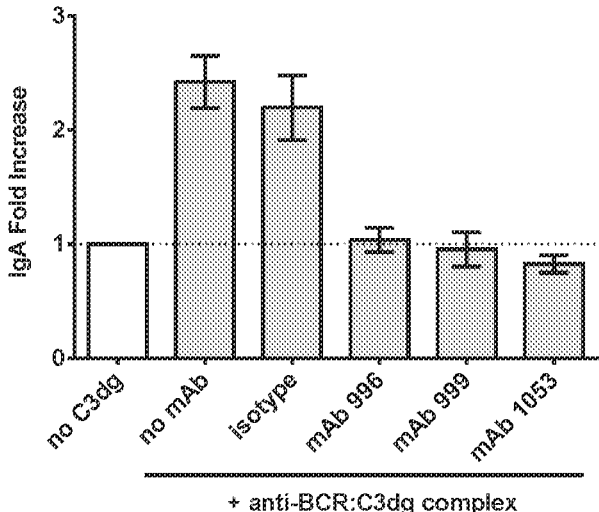

FIG. 10: demonstrates that mAb 996, mAb 999 and mAb 1053 inhibit C3dg-dependent immunoglobulin secretion from primary human B cells in a dose-dependent manner.

Figure 11:
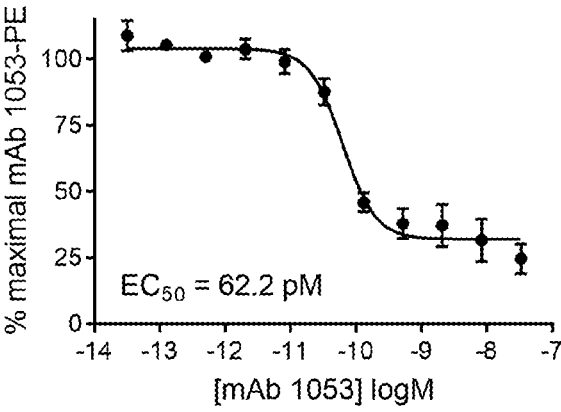

FIG. 11: demonstrates target engagement of mAb 1053 on primary human tonsil FDCs.

Figure 12:
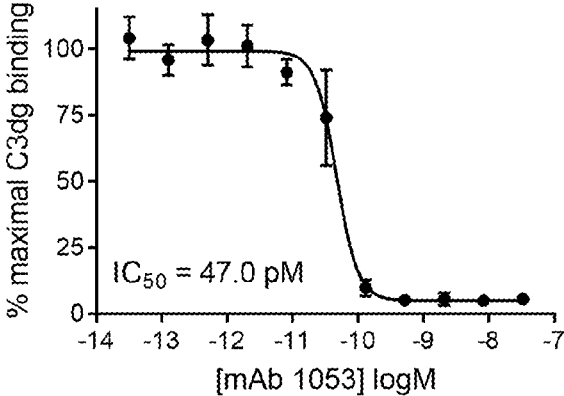

FIG. 12: demonstrates dose-dependent inhibition of model C3dg-opsonised ligand binding on primary human tonsil FDCs by mAb 1053.

DETAILED DESCRIPTION OF THE DISCLOSURE

The term "antigen binding protein" as used herein refers to antibodies and other protein constructs, such as domains, which are capable of binding to CR2. The terms "CR2 binding protein" and "antigen binding protein" and "anti-CR2 antigen binding protein" are used interchangeably herein.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanised, multispecific antibodies, including bispecific antibodies, and heteroconjugate antibodies; a single variable domain (e.g., a domain antibody (DAB)), antigen binding antibody fragments, Fab, F(ab')₂, Fv, disulphide linked Fv, single chain Fv, disulphide-linked scFv, diabodies, TAND-ABS, etc. and modified versions of any of the foregoing (for a summary of alternative "antibody" formats see Holliger and Hudson, Nature Biotechnology, 2005, Vol 23, No. 9, 1126-1136).

Alternative antibody formats include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain.

The term "domain" refers to a folded polypeptide structure which retains its tertiary structure independent of the rest of the polypeptide. Generally, domains are responsible for discrete functional properties of polypeptides and in many cases may be added, removed or transferred to other polypeptides without loss of function of the remainder of the protein and/or of the domain.

The term "single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain is capable of binding an antigen or epitope independently of a different variable region or domain. A "domain antibody" or "DAB" may be considered the same as a "single variable domain". A single variable domain may be a human single variable domain, but also includes single variable domains from other species such as rodent (for example, as disclosed in WO 00/29004 A1), nurse shark and Camelid VHH DABs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are considered to be "single variable domains". As used herein, VH includes camelid VHH domains.

An antigen binding fragment may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions.

The protein scaffold may be an Ig scaffold, for example an IgG, or IgA scaffold. The IgG scaffold may comprise some or all the domains of an antibody (i.e. CH1, CH2, CH3, VH, VL). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof.

The protein scaffold may be a derivative of a scaffold selected from the group consisting of CTLA-4, lipocalin, Protein A derived molecules such as Z-domain of Protein A (Affibody, SpA), A-domain (Avimer/Maxibody); heat shock proteins such as GroEI and GroES; transferrin (trans-body); ankyrin repeat protein (DARPin); peptide aptamer; C-type lectin domain (Tetranectin); human Y-crystallin and human ubiquitin (affilins); PDZ domains; scorpion toxin kunitz type domains of human protease inhibitors; and fibronectin/adnectin; which has been subjected to protein engineering in order to obtain binding to an antigen, such as <antigen>, other than the natural ligand.

Antigen binding site refers to a site on an antigen binding protein which is capable of specifically binding to an antigen, this may be a single variable domain, or it may be paired VH/VL domains as can be found on a standard antibody. Single-chain Fv (ScFv) domains can also provide antigen-binding sites.

The term "chimeric antigen receptor" ("CAR") as used herein, refers to an engineered receptor which consists of an extracellular antigen binding domain (which is usually derived from a monoclonal antibody, or fragment thereof, e.g. a VH domain and a VL domain in the form of a scFv), optionally a spacer region, a transmembrane region, and one or more intracellular effector domains. CARs have also been referred to as chimeric T cell receptors or chimeric immunoreceptors (CIRs). CARs are genetically introduced into hematopoietic cells, such as T cells, to redirect T cell specificity for a desired cell-surface antigen, resulting in a CAR-T therapeutic.

The term "spacer region" as used herein, refers to an oligo- or polypeptide that functions to link the transmembrane domain to the target binding domain. This region may also be referred to as a "hinge region" or "stalk region". The size of the spacer can be varied depending on the position of the target epitope in order to maintain a set distance (e.g. 14 nm) upon CAR:target binding.

The term "transmembrane domain" as used herein refers to the part of the CAR molecule which traverses the cell membrane.

The term "intracellular effector domain" (also referred to as the "signalling domain") as used herein refers to the domain in the CAR which is responsible for intracellular signalling following the binding of the antigen binding domain to the target. The intracellular effector domain is responsible for the activation of at least one of the normal effector functions of the immune cell in which the CAR is expressed. For example, the effector function of a T cell can be a cytolytic activity or helper activity including the secretion of cytokines.

It will be appreciated by a person skilled in the art that VH and/or VL domains disclosed herein may be incorporated, e.g. in the form of a scFv, into CAR-T therapeutics.

In one embodiment, CR2 binding proteins of the present disclosure show cross-reactivity between human CR2 and CR2 from another species, such as cynomolgus macaque CR2. In an embodiment, the CR2 binding proteins of the invention specifically bind human and cynomolgus macaque CR2. This is particularly useful, since drug development typically requires testing of lead drug candidates in animal systems before the drug is tested in humans. The provision of a drug that can bind human and monkey species allows one to test results in these systems and make side-by-side comparisons of data using the same drug. This avoids the complication of needing to find a drug that works against an animal CR2 and a separate drug that works against human CR2, and also avoids the need to compare results in humans and animals using non-identical drugs. Cross reactivity between other species used in disease models such as dog or mouse, is also envisaged.

Optionally, the binding affinity of the antigen binding protein for at least cynomolgus macaque CR2 and the binding affinity for human CR2 differ by no more than a factor of 2 or 5.

Affinity, also referred to as "binding affinity", is the strength of binding at a single interaction site, i.e. of one molecule, e.g. a CR2 binding protein of the invention, to another molecule, e.g. its target antigen, at a single binding site. The binding affinity of an antigen binding protein to its target may be determined by equilibrium methods (e.g. enzyme-linked immunoabsorbent assay (ELISA) or radio-immunoassay (RIA)), or kinetics (e.g. BIACORE analysis). For example, the BIACORE methods described in Example 3 may be used to measure binding affinity.

Avidity, also referred to as functional affinity, is the cumulative strength of binding at multiple interaction sites, e.g. the sum total of the strength of binding of two molecules (or more, e.g. in the case of a bispecific or multispecific molecule) to one another at multiple sites, e.g. taking into account the valency of the interaction.

In an embodiment, the equilibrium dissociation constant (KD) of the antigen binding protein-CR2 interaction is 1 nM or less. In another embodiment, the equilibrium dissociation constant (KD) of the antigen binding protein-CR2 interaction is 0.5 nM or less. Alternatively, the KD may be between 0.1 and 1 nM; or between 0.2 and 0.5 nM. A skilled person will appreciate that the smaller the KD numerical value, the stronger the binding. The reciprocal of KD (i.e. 1/KD) is the equilibrium association constant (KA) having units $M^{-1}$. A skilled person will appreciate that the larger the KA numerical value, the stronger the binding.

The dissociation rate constant (kd) or "off-rate" describes the stability of the antigen binding protein-CR2 complex, i.e. the fraction of complexes that decay per second. For example, a kd of 0.01 $s^{-1}$ equates to 1% of the complexes decaying per second. In an embodiment, the dissociation rate constant (kd) is $1\times10^{-4}$ $s^{-1}$ or less, $1\times10^{-5}$ $s^{-1}$ or less, or $1\times10^{-6}$ $s^{-1}$ or less. The kd may be between $1\times10^{-5}$ $s^{-1}$ and $1\times10^{-4}$ $s^{-1}$; or between $1\times10^{-4}$ $s^{-1}$ and $1\times10^{-3}$ $s^{-1}$.

The association rate constant (ka) or "on-rate" describes the rate of antigen binding protein-CR2 complex formation. In an embodiment, the association rate constant (ka) is $1\times10^8$ or less $M^{-1}s^{-1}$. In another embodiment the Ka may be between $1\times10^7$ and $1\times10^8$ $M^{-1}s^{-1}$.

The term "neutralises" as used throughout the present specification means that the biological activity of CR2 is reduced or blocked in the presence of an antigen binding protein as described herein in comparison to the activity of CR2 in the absence of the antigen binding protein, in vitro or in vivo. Neutralisation may be due to one or more of blocking CR2 binding to its ligand (i.e. C3d/g), preventing CR2 from being activated, down regulating CR2, or affecting effector functionality. For example, the methods described in Example 2, Example 4 and Examples 6 to 11, may be used to assess the neutralising capability of a CR2 binding protein.

The reduction or inhibition in biological activity may be partial or total. A neutralising antigen binding protein may neutralise the activity of CR2 by lowering the threshold for B cell activation by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to CR2 activity in the absence of the antigen binding protein.

Neutralisation may be determined or measured using one or more assays known to the skilled person or as described herein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and variable domain regions within full-length antigen binding sequences, e.g. within an antibody heavy chain sequence or antibody light chain sequence, are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full-length antibody sequences. There are also alternative numbering conventions for CDR sequences, for example those set out in Chothia et al. (1989) Nature 342:877-883. The structure and protein folding of the antigen binding protein may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

| | Kabat CDR | Chothia CDR | AbM CDR | Contact CDR | Minimum binding unit |
|---|---|---|---|---|---|
| H1 | 31-35/ 35A/35B | 26-32/ 33/34 | 26-35/ 35A/35B | 30-35/ 35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

Accordingly, an antigen binding protein is provided, which comprises any one or a combination of the following CDRs: CDRH1, CDRH2, CDRH3 from SEQ ID NO:5 and/or CDRL1, CDRL2, CDRL3 from SEQ ID NO:6. In another embodiment an antigen binding protein is provided, which comprises any one or a combination of the following CDRs: CDRH1, CDRH2, CDRH3 from SEQ ID NO:17 and/or CDRL1, CDRL2, CDRL3 from SEQ ID NO:18. In a further embodiment an antigen binding protein is provided, which comprises any one or a combination of the following CDRs: CDRH1, CDRH2, CDRH3 from SEQ ID NO:29 and/or CDRL1, CDRL2, CDRL3 from SEQ ID NO:30.

CDRs or minimum binding units may be modified by at least one amino acid substitution, deletion or addition, wherein the variant antigen binding protein substantially retains the biological characteristics of the unmodified protein, such as binding to CR2.

It will be appreciated that each of CDR H1, H2, H3, L1, L2, L3 may be modified alone or in combination with any other CDR, in any permutation or combination. In one embodiment, a CDR is modified by the substitution, deletion or addition of up to 3 amino acids, for example 1 or 2 amino acids, for example 1 amino acid. Typically, the modification is a substitution, particularly a conservative substitution, for example as shown in Table 2 below.

TABLE 2

| Side chain | Members |
| --- | --- |
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

For example, in a variant CDR, the amino acid residues of the minimum binding unit may remain the same, but the flanking residues that comprise the CDR as part of the Kabat or Chothia definition(s) may be substituted with a conservative amino acid residue.

Such antigen binding proteins comprising modified CDRs or minimum binding units as described above may be referred to herein as "functional CDR variants" or "functional binding unit variants".

The term "epitope" as used herein refers to that portion of the antigen that makes contact with a particular binding domain of the antigen binding protein. An epitope may be linear or conformational/discontinuous. A conformational or discontinuous epitope comprises amino acid residues that are separated by other sequences, i.e. not in a continuous sequence in the antigen's primary sequence. Particular residues comprised within an epitope can be determined through computer modelling programs or via three-dimensional structures obtained through methods known in the art, such as X-ray crystallography.

In one aspect of the invention there is provided a CR2 binding protein which binds to human CR2 at one or more amino acid residues within SEQ ID NO:2. In another embodiment there is provided a CR2 binding protein which binds to human CR2 at one or more amino acid residues within the linker between the two SCR domains of human CR2. In another embodiment of the invention there is provided a CR2 binding protein which binds to human CR2 at one or more amino acid residues within SEQ ID NO:71. In a further embodiment of the invention there is provided a CR2 binding protein which binds to human CR2 at one or more amino acid residues within SEQ ID NO: 2 and/or SEQ ID NO:71.

In another aspect of the invention there is provided a CR2 binding protein which protects residues 66 to 70 (SEQ ID NO:2) of CR2 from deuterium exchange in HDX-MS analysis, for example as described in Example 1. In a further embodiment of the invention there is provided a CR2 binding protein which protects residues 66 to 70 (SEQ ID NO:2) and/or residues 104-127 (SEQ ID NO:71) of CR2 from deuterium exchange in HDX-MS analysis, for example as described in Example 1.

Competition between the antigen binding protein of the invention and a reference antigen binding protein, e.g. a reference antibody, may be determined by competition ELISA, FMAT or BIACORE. There are several possible reasons for this competition: the two proteins may bind to the same or overlapping epitopes, there may be steric inhibition of binding, or binding of the first protein may induce a conformational change in the antigen that prevents or reduces binding of the second protein.

The invention is based on the identification of CR2 binding proteins which bind to novel epitopes of CR2 and prevent its activation. Preventing activation of CR2 will modulate the activation threshold on B cells and prevent activation and expansion of autoantibody producing B cells in response to self-antigen (a mechanism implicated in autoimmune and/or inflammatory conditions); and the retention of C3d/g opsonised antigens within FDC reservoirs will be reduced (an important mechanism implicated in viral diseases such as HIV and the generation of autoantibodies).

The antibodies and antigen-binding fragments thereof of the invention prevent the binding of C3d/g-opsonised complexes to non-cognate B cells, thereby preventing carriage and transfer of the complexes to FDCs within the germinal centre.

Some isotypes of human constant regions, in particular IgG4 and IgG2 isotypes, essentially lack the functions of a) activation of complement by the classical pathway; and b) antibody-dependent cellular cytotoxicity (ADCC). Various modifications to the heavy chain constant region of antigen binding proteins may be carried out to alter effector function depending on the desired effector property. IgG1 constant regions containing specific mutations which reduce binding to Fc receptors and reduce an effector function, such as ADCC and CDC, have been described (Duncan et al. *Nature* 1988, 332; 563-564; Lund et al. *J. Immunol.* 1991, 147; 2657-2662; Chappel et al. *PNAS* 1991, 88; 9036-9040; Burton and Woof, *Adv. Immunol.* 1992, 51; 1-84; Morgan et al., *Immunology* 1995, 86; 319-324; Hezareh et al., *J. Virol.* 2001, 75 (24); 12161-12168).

In one embodiment of the present invention there is provided a CR2 binding protein comprising a constant region such that the antigen binding protein has reduced effector function, such as reduced ADCC and/or complement dependent cytotoxic activity (CDC). In one such embodiment, the heavy chain constant region may comprise a naturally disabled constant region of an IgG2 or IgG4 isotype or a mutated IgG1 constant region. Examples of suitable modifications are described in EP 0307434. One example comprises substitution with alanines at positions 235 and 237 (EU index numbering), i.e. L235A and G237A (commonly referred to as "LAGA" mutations). Another example comprises substitution with alanines at positions 234 and 235 (EU index numbering), i.e. L234A and L235A (commonly referred to as "LALA" mutations).

Additional alterations and mutations to decrease effector function include: (with reference to IgG1 unless otherwise noted): aglycosylated N297A or N297Q or N297G; L235E; IgG4:F234A/L235A; and chimeric IgG2/IgG4. IgG2: H268Q/V309L/A330S/P331S, and IgG2: V234A/G237A/P238S/H268A/V309L/A330S/P331S can reduce FcγR and C1q binding (Wang et al. 2018 and U.S. Pat. No. 8,961,967).

Other mutations that decrease effector function include L234F/L235E/P331S; a chimeric antibody created using the CH1 and hinge region from human IgG2 and the CH2 and CH3 regions from human IgG4; IgG2m4, based on the IgG2 isotype with four key amino acid residue changes derived from IgG4 (H268Q, V309L, A330S and P331S); IgG20 which contains V234A/G237A/P238S/H268A/V309L/A330S/P331S substitutions to eliminate affinity for Fcγ receptors and C1q complement protein; IgG2m4 (H268Q/V309L/A330S/P331S, changes to IgG4); IgG4 (S228P/L234A/L235A); huIgG1 L234A/L235A (AA); huIgG4 S228P/L234A/L235A; IgG10 (L234A/L235A/G237A/P238S/H268A/A330S/P331S); IgG401 (S228P/F234A/L235A/G237A/P238S); and IgG402 (S228P/F234A/

L235A/AG236/G237A/P238S, wherein A denotes a deletion) (Tam et al., Antibodies 2017, 6 (3)).

The present invention also provides a CR2 binding protein which is human, humanised or chimeric. In one embodiment, the CR2 binding protein is human.

The present invention also provides a CR2 binding protein, comprising a heavy chain CDR3 having the amino acid sequence of SEQ ID NO:9. In one embodiment the CR2 binding protein may further comprise a heavy chain CDR2 of SEQ ID NO:8 and a heavy chain CDR1 of SEQ ID NO:7. In another embodiment the CR2 binding protein may further comprise one, two or three of a light chain CDR1 of SEQ ID NO: 10, CDR2 of SEQ ID NO: 11 and CDR3 of SEQ ID NO: 12. In a further embodiment the CR2 binding protein comprises a heavy chain CDR1 of SEQ ID NO:7, a heavy chain CDR2 of SEQ ID NO: 8, a heavy chain CDR3 of SEQ ID NO:9, a light chain CDR1 of SEQ ID NO:10, a light chain CDR2 of SEQ ID NO:11 and a light chain CDR3 of SEQ ID NO:12.

The present invention also provides a CR2 binding protein comprising a heavy chain variable region of SEQ ID NO:5. In one embodiment the CR2 binding protein may further comprise a light chain variable region of SEQ ID NO:6. In another embodiment the CR2 binding protein comprises a heavy chain variable region of SEQ ID NO:5 and a light chain variable region of SEQ ID NO:6.

The present invention also provides a CR2 binding protein comprising a heavy chain variable region selected from an amino acid sequence having 75% or greater, 80% or greater, 85% or greater, 90% or greater, 95% or greater, 98% or greater, 99% or greater identity or 100% identity to the amino acid sequence of SEQ ID NO:5, and a light chain variable region selected from an amino acid sequence having 75% or greater, 80% or greater, 85% or greater, 90% or greater, 95% or greater, 98% or greater, 99% or greater or 100% identity to the amino acid sequence of SEQ ID NO:6. In one embodiment, the CR2 binding protein comprises a heavy chain variable region having 98% or greater identity to the amino acid sequence of SEQ ID NO:5 and a light chain variable region having 98% identity to the amino acid sequence of SEQ ID NO:6. In a further embodiment, the CR2 binding protein comprises a heavy chain of SEQ ID NO:3 and a light chain of SEQ ID NO:4 (mAb 1053 which is CHO-expressed material unless stated otherwise).

The present invention also provides a CR2 binding protein, comprising a heavy chain CDR3 having the amino acid sequence of SEQ ID NO:21. In one embodiment, the CR2 binding protein may further comprise a heavy chain CDR2 of SEQ ID NO:20 and a heavy chain CDR1 of SEQ ID NO:19. In another embodiment, the CR2 binding protein may further comprise one, two or three of a light chain CDR1 of SEQ ID NO: 22, CDR2 of SEQ ID NO: 23 and CDR3 of SEQ ID NO:24. In a further embodiment, the CR2 binding protein comprises a heavy chain CDR1 of SEQ ID NO: 19, a heavy chain CDR2 of SEQ ID NO: 20, a heavy chain CDR3 of SEQ ID NO:21, a light chain CDR1 of SEQ ID NO:22, a light chain CDR2 of SEQ ID NO:23 and a light chain CDR3 of SEQ ID NO:24.

The present invention also provides a CR2 binding protein comprising a heavy chain variable region of SEQ ID NO:17. In one embodiment the CR2 binding protein may further comprise a light chain variable region of SEQ ID NO: 18. In another embodiment, the CR2 binding protein comprises a heavy chain variable region of SEQ ID NO: 17 and a light chain variable region of SEQ ID NO: 18.

The present invention also provides a CR2 binding protein comprising a heavy chain variable region selected from an amino acid sequence having 75% or greater, 80% or greater, 85% or greater, 90% or greater, 95% or greater, 98% or greater, 99% or greater identity or 100% identity to the amino acid sequence of SEQ ID NO:17, and a light chain variable region selected from an amino acid sequence having 75% or greater, 80% or greater, 85% or greater, 90% or greater, 95% or greater, 98% or greater, 99% or greater or 100% identity to the amino acid sequence of SEQ ID NO:18. In one embodiment, the CR2 binding protein comprises a heavy chain variable region having 98% or greater identity to the amino acid sequence of SEQ ID NO: 17 and a light chain variable region having 98% identity to the amino acid sequence of SEQ ID NO: 18. In a further embodiment, embodiment the CR2 binding protein comprises a heavy chain of SEQ ID NO: 15 and a light chain of SEQ ID NO:16 (mAb 996 which is CHO-expressed material unless stated otherwise).

The present invention also provides a CR2 binding protein, comprising a heavy chain CDR3 having the amino acid sequence of SEQ ID NO:33. In one embodiment the CR2 binding protein may further comprise a heavy chain CDR2 of SEQ ID NO:32 and a heavy chain CDR1 of SEQ ID NO:31. In another embodiment the CR2 binding protein may further comprise one, two or three of a light chain CDR1 of SEQ ID NO:34, CDR2 of SEQ ID NO:35 and CDR3 of SEQ ID NO:36. In a further embodiment the CR2 binding protein comprises a heavy chain CDR1 of SEQ ID NO:31, a heavy chain CDR2 of SEQ ID NO: 32, a heavy chain CDR3 of SEQ ID NO:33, a light chain CDR1 of SEQ ID NO:34, a light chain CDR2 of SEQ ID NO:35 and a light chain CDR3 of SEQ ID NO:36.

The present invention also provides a CR2 binding protein comprising a heavy chain variable region of SEQ ID NO:29. In one embodiment the CR2 binding protein may further comprise a light chain variable region of SEQ ID NO:30. In another embodiment the antibody or antigen-binding fragment comprises a heavy chain variable region of SEQ ID NO:29 and a light chain variable region of SEQ ID NO:30.

The present invention also provides a CR2 binding protein comprising a heavy chain variable region selected from an amino acid sequence having 75% or greater, 80% or greater, 85% or greater, 90% or greater, 95% or greater, 98% or greater, 99% or greater identity or 100% identity to the amino acid sequence of SEQ ID NO:29, and a light chain variable region selected from an amino acid sequence having 75% or greater, 80% or greater, 85% or greater, 90% or greater, 95% or greater, 98% or greater, 99% or greater or 100% identity to the amino acid sequence of SEQ ID NO:30. In one embodiment the CR2 binding protein comprises a heavy chain variable region having 98% or greater identity to the amino acid sequence of SEQ ID NO:29 and a light chain variable region having 98% identity to the amino acid sequence of SEQ ID NO:30. In a further embodiment, the CR2 binding protein comprises a heavy chain of SEQ ID NO:27 and a light chain of SEQ ID NO:28 (mAb 999 which is CHO-expressed material unless stated otherwise).

The disclosure herein contemplates a CR2 binding protein comprising any and all combinations of such heavy and light chain variable regions.

The present invention also provides nucleic acid molecules encoding CR2 binding proteins. In one embodiment there is provided a nucleic acid sequence of SEQ ID NO:13. In another embodiment there is provided a nucleic acid sequence of SEQ ID NO: 14. In another embodiment there is provided a nucleic acid sequence of SEQ ID NO:25. In another embodiment there is provided a nucleic acid sequence of SEQ ID NO:26. In another embodiment there is provided a nucleic acid sequence of SEQ ID NO: 37. In a further embodiment there is provided a nucleic acid sequence of SEQ ID NO:38.

The present invention also provides an expression vector comprising a nucleic acid molecule described herein encoding a heavy chain and/or a light chain of the CR2 binding proteins described herein. In one embodiment, the same vector includes the nucleic acid sequences of the heavy chain and the light chain. In another embodiment, separate vectors include the nucleic acid sequences of the heavy chain and the light chain, i.e. one vector encodes the heavy chain and another vector encodes the light chain. In one embodiment there is provided an expression vector comprising a nucleic acid sequence of SEQ ID NO:13. In another embodiment there is provided an expression vector comprising a nucleic acid sequence of SEQ ID NO: 14. In another embodiment there is provided an expression vector comprising a nucleic acid sequence of SEQ ID NO:25. In another embodiment there is provided an expression vector comprising a nucleic acid sequence of SEQ ID NO:26. In another embodiment there is provided an expression vector comprising a nucleic acid sequence of SEQ ID NO: 37. In a further embodiment there is provided an expression vector comprising a nucleic acid sequence of SEQ ID NO:38.

Further, the present invention provides a recombinant host cell containing such an expression vector(s) and capable of expressing said CR2 binding proteins. In one embodiment there is provided a recombinant host cell containing an expression vector comprising a nucleic acid sequence of SEQ ID NO: 13. In another embodiment there is provided a recombinant host cell containing an expression vector comprising a nucleic acid sequence of SEQ ID NO: 14. In another embodiment there is provided a recombinant host cell containing an expression vector comprising a nucleic acid sequence of SEQ ID NO: 25. In another embodiment there is provided a recombinant host cell containing an expression vector comprising a nucleic acid sequence of SEQ ID NO:26. In another embodiment there is provided a recombinant host cell containing an expression vector comprising a nucleic acid sequence of SEQ ID NO: 37. In a further embodiment there is provided a recombinant host cell containing an expression vector comprising a nucleic acid sequence of SEQ ID NO:38.

The present invention also provides a CR2 binding protein expressed by a recombinant host cell as described herein.

The sequences disclosed, SEQ ID NO: 1 to 74 are defined according to Kabat unless otherwise stated.

The examples hereinafter, describe a range of assays on primary human B cells which were developed to understand the impact of the antibodies and antigen-binding fragments thereof of the invention on human biology. Collectively, these data provide experimental evidence to support that the CR2 binding proteins of the invention effectively inhibit CR2-dependent mechanisms of autoimmunity on B cells.

In one embodiment of the present invention there is provided a CR2 binding protein, which inhibits opsonised autoantigen carriage on non-conjugate B cells by preventing binding of pre-bound opsonised complexes. In another embodiment of the present invention there is provided a CR2 binding protein, which inhibits opsonised autoantigen carriage on non-conjugate B cells by competition with pre-bound opsonised complexes. In another embodiment of the present invention there is provided a CR2 binding protein, which prevents B cell activation by opsonised autoantigen. In another embodiment of the present invention there is provided a CR2 binding protein, which inhibits calcium flux in human B cells. In another embodiment of the present invention there is provided a CR2 binding protein, which inhibits phosphoprotein signalling in human B cells. In a further embodiment, there is provided a CR2 binding protein, which inhibits CR2-dependent CD69 upregulation in human B cells.

Statement of Use

The present invention thus provides CR2 binding proteins for use in therapy. In one embodiment the CR2 binding proteins can be used in the treatment of diseases or conditions for which a CR2 inhibitor is indicated.

In one embodiment there is provided a CR2 binding protein for use in the treatment of a disease in which B cell activation is implicated. In another embodiment there is provided the use of a CR2 binding protein in the manufacture of a medicament for use in the treatment of a disease in which B cell activation is implicated. In a further embodiment there is provided a method for the treatment of a disease in which B cell activation is implicated in a subject in need thereof, comprising administering to said subject a therapeutically effective amount of a CR2 binding protein.

In one embodiment there is provided a CR2 binding protein for use in the treatment of a disease associated with retention of C3d or C3dg opsonised antigens within a FDC reservoir. In another embodiment there is provided the use of a CR2 binding protein in the manufacture of a medicament for use in the treatment of a disease associated with retention of C3d or C3dg opsonised antigens within a FDC reservoir. In a further embodiment there is provided a method for the treatment of a disease associated with retention of C3d or C3dg opsonised antigens within an FDC reservoir in a subject in need thereof, comprising the step of administering to said subject a therapeutically effective amount of a CR2 binding protein.

AutoImmune and/or Inflammatory Conditions

Due to the role of CR2 in the generation/maintenance of germinal centre reactions, the blockade of this mechanism is expected to be effective in the treatment of autoimmune and/or inflammatory conditions such as Sjögren's syndrome, systemic lupus erythematosus and rheumatoid arthritis. Furthermore, patients with Sjögren's syndrome, systemic lupus erythematosus or rheumatoid arthritis, have been found to contain circulating immune complexes bearing C3b/iC3b or C3d.

Given that CR2 plays an important role in reducing the threshold for B cell activation, and promoting antibody production, CR2 blockade offers an excellent opportunity to re-set B cell mediated pathology.

Sjögren's syndrome is an autoimmune rheumatic disease, in which lymphocytic infiltration of the tissues leads to exocrine gland secretory dysfunction and multi-system inflammation. Disease severity is closely associated with B cell activation, circulating autoantibodies and a high frequency of germinal centre foci in exocrine tissue. A subgroup of Sjögren's syndrome patients with high disease activity and widespread autoantibody production have low levels of complement C3, suggesting consumption through increased complement activation that may contribute to pathogenicity in Sjögren's syndrome.

SLE is a chronic autoimmune disease and its pathogenesis is unknown. There is no cure for SLE, treatment involves preventing flares and reducing their severity and duration when they occur. Treatments include corticosteroids, cytotoxic drugs such as cyclophosphamide, hydroxychloroquine and belimumab.

CR2 has been implicated in the pathogenesis of SLE and a number of reports have suggested that CR2 plays a critical role in the recognition of foreign DNA during the host-immune response. This recognition function may be a mechanism that influences the development of autoimmunity to DNA in SLE.

The activation of different parts of the complement cascade in RA has been known for a long time. For example, levels of the CR2 ligand, C3d/g are elevated in the synovial fluids of RA patients. Studies have also demonstrated the presence of CR2 on fibroblast-like synoviocytes (FLS) in the inflamed synovium of patients with rheumatoid arthritis (RA).

CR2 binding proteins may be useful in the treatment of a wide variety of autoimmune and/or inflammatory conditions including but not limited to rheumatoid arthritis (RA), Sjögren's syndrome, systemic lupus erythematosus (SLE, for example lupus nephritis), vasculitis (for example anti-neutrophil cytoplasmic antibody (ANCA)-associated vasculitis, systemic necrotizing vasculitis, polyarteritis nodosa, allergic angiitis and granulomatosis, polyangiitis, Wegener's granulomatosis, lymphomatoid granulomatosis, giant cell arteritis, mucocutaneous lymph node syndrome (MLNS or Kawasaki's disease), isolated CNS vasculitis, Behcet's disease, thromboangiitis obliterans (Buerger's disease) and cutaneous necrotizing venulitis) idiopathic membranous glomerulonephritis, myasthenia gravis, pemphigus, scleroderma, systemic sclerosis, anti-glomerular basement membrane disease, bullous pemphigoid, multiple sclerosis, neuromyelitis optica, meningitis; encephalitis, haemophilia inhibitors, antibodies to enzyme replacement therapy, IgA nephropathy, polymyositis, dermatomyositis, Graves' disease (for example, autoimmune thyroiditis and Hashimoto disease), antiphospholipid syndrome, type 1 diabetes mellitus, autoimmune hemolytic anemia, idiopathic thrombocytopenia purpura, solid organ transplant, autoimmune pulmonary alveolar proteinosis. uveitis; osteoarthritis, autoimmune hemolytic anemia (for example autoimmune hemolytic anemia, immune pancytopenia, and paroxysmal nocturnal hemoglobinuria), autoimmune chronic active hepatitis, primary biliary cirrhosis, granulomatous hepatitis, sclerosing cholangitis and antigen-antibody complex mediated diseases (for example inflammations of the lung, pleurisy, alveolitis, vasculitis, pneumonia, chronic bronchitis, bronchiectasis, diffuse pan bronchiolitis, hypersensitivity pneumonitis and idiopathic pulmonary fibrosis (IPF)).

In one embodiment the autoimmune and/or inflammatory condition is selected from rheumatoid arthritis (RA), Sjögren's syndrome, systemic lupus erythematosus (SLE) and vasculitis. In another embodiment the autoimmune and/or inflammatory condition is rheumatoid arthritis (RA). In another embodiment the autoimmune and/or inflammatory condition is Sjögren's syndrome. In another embodiment the autoimmune and/or inflammatory condition is systemic lupus erythematosus (SLE). In another embodiment the autoimmune and/or inflammatory condition is vasculitis. In a further embodiment the autoimmune and/or inflammatory condition is anti-neutrophil cytoplasmic antibody (ANCA)-associated vasculitis.

In one embodiment there is provided a CR2 binding protein for use in the treatment of an autoimmune and/or inflammatory condition. In another embodiment there is provided a CR2 binding protein for use in the treatment of rheumatoid arthritis (RA). In another embodiment there is provided a CR2 binding protein for use in the treatment of Sjögren's syndrome. In another embodiment there is provided a CR2 binding protein for use in the treatment of systemic lupus erythematosus (SLE). In another embodiment there is provided a CR2 binding protein for use in the treatment of vasculitis. In another embodiment there is provided a CR2 binding protein for use in the treatment of anti-neutrophil cytoplasmic antibody (ANCA)-associated vasculitis.

In one embodiment there is provided the use of a CR2 binding protein in the manufacture of a medicament for the treatment of an autoimmune and/or inflammatory condition. In another embodiment there is provided the use of a CR2 binding protein in the manufacture of a medicament for the treatment of rheumatoid arthritis (RA). In another embodiment there is provided the use of a CR2 binding protein in the manufacture of a medicament for the treatment of Sjögren's syndrome. In another embodiment there is provided the use of a CR2 binding protein in the manufacture of a medicament for the treatment of systemic lupus erythematosus (SLE). In another embodiment there is provided the use of a CR2 binding protein in the manufacture of a medicament for the treatment of vasculitis. In another embodiment there is provided the use of a CR2 binding protein in the manufacture of a medicament for the treatment of anti-neutrophil cytoplasmic antibody (ANCA)-associated vasculitis.

Also provided is a method for treatment of an autoimmune and/or inflammatory condition in a subject in need thereof, comprising administering to said subject a therapeutically effective amount of a CR2 binding protein. In another embodiment there is provided a method for treatment of rheumatoid arthritis (RA) in a subject in need thereof, comprising administering to said subject a therapeutically effective amount of a CR2 binding protein. In another embodiment, there is provided a method for the treatment of Sjögren's syndrome in a subject in need thereof, comprising administering to said subject a therapeutically effective amount of a CR2 binding protein. In another embodiment, there is provided a method for the treatment of systemic lupus erythematosus (SLE) in a subject in need thereof, comprising administering to said subject a therapeutically effective amount of a CR2 binding protein. In another embodiment, there is provided a method for the treatment of vasculitis in a subject in need thereof, comprising administering to said subject a therapeutically effective amount of a CR2 binding protein. In a further embodiment, there is provided a method for the treatment of anti-neutrophil cytoplasmic antibody (ANCA)-associated vasculitis in a subject in need thereof, comprising administering to said subject a therapeutically effective amount of a CR2 binding protein. Suitably the subject in need thereof is a mammal, particularly a human.

Infectious Diseases

Many viral diseases, for example HIV, are difficult to treat due to the persistence of long-lived viral reservoirs such as in FDCs in lymphatic tissue. Antigen binding, retention in excess of one year, and presentation are largely dependent on the CR2-dependent capture of C3 fragment-coated antigens. C3d/g-opsonised HIV virions are captured and retained long-term in non-degradative endosomes, representing a long-lived viral reservoir.

Current HIV treatments with combination antiretroviral therapy (CART) effectively prevents viral spread and HIV disease but does not lead to viral eradication due to the persistence of long-lived viral reservoirs comprising latently HIV-infected cells and anatomic or physiological sites that can retain replication competent virus able to persist for years.

Virus trapped by FDCs represents a critical mechanism for the replenishment of the reservoir by creating a persistent source of infectious virus within lymphoid tissues, which may cause new rounds of infection and viral recrudescence after cessation of CART, preventing long-term viral remission and HIV cure.

CR2 binding proteins may be useful in the treatment, prevention or reactivation of infectious diseases including but not limited to human immunodeficiency virus (HIV), hepatitis (A, B, C, D and E) and Epstein-Barr Virus (EBV)), bacterial infection, fungal infections, protozoal infections and parasitic infections.

In one embodiment, there is provided a CR2 binding protein for use in the treatment or prevention of an infectious disease. In another embodiment, there is provided a CR2 binding protein for use in the treatment or prevention of a viral infection. In another embodiment, there is provided a CR2 binding protein for use in the treatment or prevention of HIV. In another embodiment, there is provided a CR2 binding protein for use in the treatment or prevention of AIDS. In another embodiment, there is provided a CR2 binding protein for use in the treatment or prevention of hepatitis A. In another embodiment, there is provided a CR2 binding protein for use in the treatment of hepatitis B. In another embodiment, there is provided a CR2 binding protein for use in the treatment or prevention of hepatitis C. In another embodiment, there is provided a CR2 binding protein for use in the treatment or prevention of hepatitis D. In another embodiment, there is provided a CR2 binding protein for use in the treatment or prevention of hepatitis E. In another embodiment, there is provided a CR2 binding protein for use in the treatment or prevention of a bacterial infection. In another embodiment, there is provided a CR2 binding protein for use in the treatment or prevention of a fungal infection. In another embodiment, there is provided a CR2 binding protein for use in the treatment or prevention of a protozoal infection. In a further embodiment, there is provided a CR2 binding protein for use in the treatment or prevention of a parasitic infection.

In one embodiment, there is provided the use of a CR2 binding protein in the manufacture of a medicament for the treatment or prevention of an infectious disease. In another embodiment, there is provided the use of a CR2 binding protein in the manufacture of a medicament for the treatment or prevention of a viral infection. In another embodiment, there is provided the use of a CR2 binding protein in the manufacture of a medicament for the treatment or prevention of HIV. In another embodiment, there is provided the use of a CR2 binding protein in the manufacture of a medicament for the treatment or prevention of AIDs. In another embodiment, there is provided the use of a CR2 binding protein in the manufacture of a medicament for the treatment or prevention of hepatitis A. In another embodiment, there is provided the use of a CR2 binding protein in the manufacture of a medicament for the treatment or prevention of hepatitis B. In another embodiment, there is provided the use of a CR2 binding protein in the manufacture of a medicament for the treatment or prevention of hepatitis C. In another embodiment, there is provided the use of a CR2 binding protein in the manufacture of a medicament for the treatment or prevention of hepatitis D. In another embodiment, there is provided the use of a CR2 binding protein in the manufacture of a medicament for the treatment or prevention of hepatitis E. In another embodiment, there is provided the use of a CR2 binding protein in the manufacture of a medicament for the treatment or prevention of a bacterial infection. In another embodiment, there is provided the use of a CR2 binding protein in the manufacture of a medicament for the treatment or prevention of a fungal infection. In another embodiment, there is provided the use of a CR2 binding protein in the manufacture of a medicament for the treatment or prevention of a protozoal infection. In a further embodiment, there is provided the use of a CR2 binding protein in the manufacture of a medicament for the treatment or prevention of a parasitic infection.

Also provided is a method for the treatment or prevention of an infectious disease in a subject in need thereof, comprising administering to said subject a therapeutically effective amount of a CR2 binding protein. In one embodiment there is provided a method for the treatment or prevention of an viral disease in a subject in need thereof, comprising administering to said subject a therapeutically effective amount of a CR2 binding protein. In another embodiment, there is provided a method for the treatment or prevention of HIV in a subject in need thereof, comprising administering to said subject a therapeutically effective amount of a CR2 binding protein. In another embodiment, there is provided a method for the treatment or prevention of AIDs in a subject in need thereof, comprising administering to said subject a therapeutically effective amount of an CR2 binding protein. In another embodiment, there is provided a method for the treatment or prevention of hepatitis A in a subject in need thereof, comprising administering to said subject a therapeutically effective amount of an CR2 binding protein. In another embodiment, there is provided a method for the treatment or prevention of hepatitis B in a subject in need thereof, comprising administering to said subject a therapeutically effective amount of an CR2 binding protein. In another embodiment, there is provided a method for the treatment or prevention of hepatitis C in a subject in need thereof, comprising administering to said subject a therapeutically effective amount of an CR2 binding protein. In another embodiment, there is provided a method for the treatment or prevention of hepatitis D in a subject in need thereof, comprising administering to said subject a therapeutically effective amount of an CR2 binding protein. In another embodiment, there is provided a method for the treatment or prevention of hepatitis E in a subject in need thereof, comprising administering to said subject a therapeutically effective amount of an CR2 binding protein. In another embodiment, there is provided a method for the treatment or prevention of a bacterial infection in a subject in need thereof, comprising administering to said subject a therapeutically effective amount of an CR2 binding protein. In another embodiment, there is provided a method for the treatment or prevention of a fungal infection in a subject in need thereof, comprising administering to said subject a therapeutically effective amount of an CR2 binding protein. In another embodiment, there is provided a method for the treatment or prevention of a protozoal infection in a subject in need thereof, comprising administering to said subject a therapeutically effective amount of an CR2 binding protein. In a further embodiment, there is provided a method for the treatment or prevention of a parasitic infection in a subject in need thereof, comprising administering to said subject a therapeutically effective amount of an CR2 binding protein. Suitably the subject in need thereof is a mammal, particularly a human.

Use as a Vaccine Adjuvant

Low doses of antigen coupled to anti-CR2 antibodies have been found to induce rapid and enduring IgG immune responses in mice and cynomolgus monkeys (Whipple, E. C. et al., Mol. Immunol., 2007. 44 (4): 377-388). In one embodiment, there is provided a CR2 binding protein for use as an adjuvant/antigen carrier to amplify immune responses to immunisation. In another embodiment, there is provided the use of a CR2 binding protein in the manufacture of a medicament for the amplification of an immune response to an immunisation. In a further embodiment, there is provided a method for the amplification of an immune response to an immunisation in a subject in need thereof, comprising administering to said subject a therapeutically effective amount of a CR2 binding protein. Suitably the subject in need thereof is a mammal, particularly a human.

Malignancies Associated with Epstein-Barr Virus (EBV)

CR2 has been identified as the major co-receptor for Epstein-Barr virus infection and therefore, may play a role in the initiation of EBV driven lymphoproliferative disease (N. Neparidze et al.; *Clinical Advances in Hematology & Oncology*, 12 (6); June 2014:358-371).

The present invention provides a CR2 binding protein for use in the treatment or prevention of a malignancy associated with EBV. The present invention also provides the use of a CR2 binding protein in the manufacture of a medicament for the treatment or prevention of a malignancy associated with EBV. The present invention also provides a method for the treatment or prevention of a malignancy associated with EBV in a subject in need thereof, comprising administering to said subject a therapeutically effective amount of a CR2 binding protein.

The present invention also provides a CR2 binding protein for use in the treatment or prevention of a malignancy associated with EBV selected from B-cell lymphoproliferative disorders, T/Natural Killer-cell lymphoproliferative disorders and epithelial malignancies.

In one embodiment the present invention provides a CR2 binding protein for use in the treatment or prevention of a B-cell lymphoproliferative disorder. In another embodiment the present invention provides a CR2 binding protein for use in the treatment or prevention of a B-cell lymphoproliferative disorder selected from FDC sarcoma, Burkitt lymphoma, Hodgkin lymphoma, post-transplant lymphoproliferative disorder, HIV-associated non-Hodgkin lymphoma, diffuse large B-cell lymphoma, immunoblastic-plasmacytoid, centroblastic, Burkitt lymphoma, primary central nervous system lymphoma, primary effusion lymphoma and its solid variant, plasmablastic lymphoma of the oral cavity type, EBV-positive diffuse large B-cell lymphoma (DLBCL) of the elderly, lymphomatoid granulomatosis and DLBCL associated with chronic inflammation.

In one embodiment the present invention provides a CR2 binding protein for use in the treatment or prevention of a T/Natural Killer-cell lymphoproliferative disorder. In another embodiment the present invention provides a CR2 binding protein for use in the treatment or prevention of a T/Natural Killer-cell lymphoproliferative disorder selected from extranodal nasal-type NK/T-cell lymphoma, aggressive NK-cell leukemia/lymphoma, angioimmunoblastic T-cell lymphoma, enteropathy-type T-cell lymphoma, EBV-associated cutaneous T-cell lymphoproliferative disorder, γδ T-cell lymphoma (hepatosplenic and nonhepatosplenic), peripheral T-cell lymphoma and T-cell lymphoproliferative disorders after chronic EBV infection.

In one embodiment the present invention provides a CR2 binding protein for use in the treatment or prevention of a epithelial malignancy. In another embodiment the present invention provides a CR2 binding protein for use in the treatment or prevention of a epithelial malignancy selected from nasopharyngeal carcinoma and gastric cancer.

The present invention also provides the use of a CR2 binding protein in the manufacture of a medicament for the treatment or prevention of a malignancy associated with EBV selected from B-cell lymphoproliferative disorders, T/Natural Killer-cell lymphoproliferative disorders and epithelial malignancies.

In one embodiment the present invention provides the use of a CR2 binding protein in the manufacture of a medicament for the treatment or prevention of a B-cell lymphoproliferative disorder. In another embodiment the present invention provides the use of a CR2 binding protein in the manufacture of a medicament for the treatment or prevention of a B-cell lymphoproliferative disorder selected from FDC sarcoma, Burkitt lymphoma, Hodgkin lymphoma, post-transplant lymphoproliferative disorder, HIV-associated non-Hodgkin lymphoma, diffuse large B-cell lymphoma, immunoblastic-plasmacytoid, centroblastic, Burkitt lymphoma, primary central nervous system lymphoma, primary effusion lymphoma and its solid variant, plasmablastic lymphoma of the oral cavity type, EBV-positive diffuse large B-cell lymphoma (DLBCL) of the elderly, lymphomatoid granulomatosis and DLBCL associated with chronic inflammation.

In one embodiment the present invention provides the use of a CR2 binding protein in the manufacture of a medicament for the treatment or prevention of a T/Natural Killer-cell lymphoproliferative disorder. In another embodiment the present invention provides the use of a CR2 binding protein in the manufacture of a medicament for the treatment or prevention of a T/Natural Killer-cell lymphoproliferative disorder selected from extranodal nasal-type NK/T-cell lymphoma, aggressive NK-cell leukemia/lymphoma, angioimmunoblastic T-cell lymphoma, enteropathy-type T-cell lymphoma, EBV-associated cutaneous T-cell lymphoproliferative disorder, γδ T-cell lymphoma (hepatosplenic and nonhepatosplenic), peripheral T-cell lymphoma and T-cell lymphoproliferative disorders after chronic EBV infection.

In one embodiment the present invention provides the use of a CR2 binding protein in the manufacture of a medicament for the treatment or prevention of a epithelial malignancy. In another embodiment the present invention provides the use of a CR2 binding protein in the manufacture of a medicament for the treatment or prevention of a epithelial malignancy selected from nasopharyngeal carcinoma and gastric cancer.

The present invention also provides a method for the treatment or prevention of a malignancy associated with EBV selected from B-cell lymphoproliferative disorders, T/Natural Killer-cell lymphoproliferative disorders and epithelial malignancies, in a subject in need thereof, comprising administering to said subject a therapeutically effective amount of a CR2 binding protein.

In one embodiment the present invention provides a method for the treatment or prevention of a B-cell lymphoproliferative disorder in a subject in need thereof, comprising administering to said subject a therapeutically effective amount of a CR2 binding protein. In another embodiment the present invention provides a method for the treatment or prevention of a B-cell lymphoproliferative disorder selected from FDC sarcoma, Burkitt lymphoma, Hodgkin lymphoma, post-transplant lymphoproliferative disorder, HIV-associated non-Hodgkin lymphoma, diffuse large B-cell lymphoma, immunoblastic-plasmacytoid, centroblastic, Burkitt lymphoma, primary central nervous system lymphoma, primary effusion lymphoma and its solid variant, plasmablastic lymphoma of the oral cavity type, EBV-positive diffuse large B-cell lymphoma (DLBCL) of the elderly, lymphomatoid granulomatosis and DLBCL associated with chronic inflammation, in a subject in need thereof, comprising administering to said subject a therapeutically effective amount of a CR2 binding protein.

In one embodiment the present invention provides a method for the treatment or prevention of a T/Natural Killer-cell lymphoproliferative disorder in a subject in need thereof, comprising administering to said subject a therapeutically effective amount of a CR2 binding protein. In another embodiment the present invention provides a method for the treatment or prevention of a T/Natural Killer-cell lymphoproliferative disorder selected from extranodal nasal-type NK/T-cell lymphoma, aggressive NK-cell leukemia/lymphoma, angioimmunoblastic T-cell lymphoma, enteropathy-type T-cell lymphoma, EBV-associated cutaneous T-cell lymphoproliferative disorder, γδ T-cell lymphoma (hepatosplenic and nonhepatosplenic), peripheral T-cell lymphoma and T-cell lymphoproliferative disorders after chronic EBV infection, in a subject in need thereof, comprising administering to said subject a therapeutically effective amount of a CR2 binding protein.

In one embodiment the present invention provides a method for the treatment or prevention of a epithelial malignancy in a subject in need thereof, comprising administering to said subject a therapeutically effective amount of a CR2 binding protein. In another embodiment the present invention provides a method for the treatment or prevention of a epithelial malignancy selected from nasopharyngeal carcinoma and gastric cancer, in a subject in need thereof, comprising administering to said subject a therapeutically effective amount of a CR2 binding protein.

Suitably the subject in need thereof is a mammal, particularly a human.

Pharmaceutical Compositions/Routes of Administration/Dosages

Pharmaceutical compositions of the invention may be used for therapeutic or prophylactic applications. In one embodiment of the invention there is provided a pharmaceutical composition comprising an CR2 binding protein and a pharmaceutically acceptable carrier or excipient thereof. In another embodiment, there is provided a pharmaceutical composition comprising 1-500 mg of a CR2 binding protein. In another embodiment, there is provided a pharmaceutical composition comprising 20-300 mg of a CR2 binding protein. In another embodiment, there is provided a pharmaceutical composition comprising 50-200 mg of a CR2 binding protein. In a further embodiment, there is provided a pharmaceutical composition comprising 50-200 mg of a CR2 binding protein which is an antibody comprising a light chain amino acid sequence as set out in SEQ ID NO:4 and a heavy chain amino acid sequence as set out in SEQ ID NO:3.

In a preferred embodiment, the pharmaceutical composition comprises a composition for parenteral, transdermal, intraluminal, intraarterial, intrathecal and/or intranasal administration or by direct injection into tissue. It is envisaged that said pharmaceutical composition is administered to a patient via infusion or injection. Administration of the suitable compositions may be effected by different ways, e.g., by intravenous, intraperitoneal, subcutaneous, intramuscular, topical or intradermal administration. In one embodiment, there is provided a pharmaceutical composition comprising an CR2 binding protein for intravenous administration. In another embodiment, there is provided a pharmaceutical composition comprising an CR2 binding protein for subcutaneous administration.

These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the compound to be administered, sex, time and route of administration, general health, and other drugs being administered concurrently.

EXAMPLES

Abbreviations

ADCC antibody-dependent cytotoxicity
Ag antigen
Akt protein kinase B
ANCA anti-neutrophilic cytoplasmic antibody
APC Allophycocyanin
BCR B cell receptor
CART combination antiretroviral therapy
CDC complement dependent cytotoxicity
CDR complementarity determining regions
CD20 B-lymphocyte antigen CD20
CHO Chinese hamster ovary cells
cIEF capillary iso-electric focussing
CL clearance
CR1 complement receptor 1
CR2 complement receptor 2
$CO_2$ carbon dioxide
CTL cytotoxic T lymphocytes
Cyno cynomolgus macaque
DLS dynamic light scattering
DMARD disease modifying anti-rheumatic drugs
DME drug metabolizing enzyme
DP drug product
DNA deoxyribonucleic acid
EBV Epstein-Barr virus
ELS ectopic lymphoid structures
ERKs extracellular signal-regulated kinases
FDC follicular dendritic cell
FITC fluorescein isothiocyanate
FLS fibroblast-like synoviocytes
GC germinal centre
hCD2 humanised CR2
HEK human embryonic kidney cells
HDX hydrogen deuterium exchange
HDMS high definition mass spectrometry
HIV human immunodeficiency virus
HPLC high performance liquid chromatography
IgG immunoglobulin G
IgM immunoglobulin M
IV intravenous
KO knockout
LC-MS liquid chromatograph mass spectrometry
mAb monoclonal antibody
MFI mean fluorescence intensity
Mg/Kg milligrams per kilogram
MRT mean residence time
MS mass spectrometry
MSD meso scale discovery
MSX methionine sulfoxamine
MW molecular weight
MZ marginal zone
NaCl sodium chloride
NaOH sodium hydroxide
NB no binding
ng/mL nano grams per millilitre NHL non-Hodgkin B-cell lymphoma
NHS normal human serum
PBS phosphate buffered saline
PBMCs human peripheral mononuclear cells
PBPK physiologically based pharmacokinetic
PLGS proteinLynx global server
PMA phorbol myristate acetate
PnPS14 pneumococcal polysaccharide 14
RA rheumatoid arthritis
S/C subcutaneous
SAD single ascending dose
SCR short consensus repeat
sCR2 soluble CR2
SCS subcapsular sinus
SEC-HPLC size exclusion chromatography-high performance liquid chromatography
SEM standard error of the mean
SLE systemic lupus erythematosus
SPR surface plasmon resonance
$t_{1/2}$ half-life
TA target engagement
TCEP tris(2-carboxyethyl) phosphine
TCR tissue cross reactivity
TFA trifluoroacetic acid
TFF tangential flow filtration
Tfh T follicular helper
Th T helper
TLR toll like receptor
TMDD target mediated drug disposition
Tox toxicology
UPLC ultra performance liquid chromatography

Example 1 HDX Epitope Mapping-CR2 Verses mAb 1053

HDX-MS analysis was performed to investigate the differential deuteration of CR2 (SCR1 & 2 domains) in the presence and absence of the mAb 1053 (CHO-expressed).
Instrumentation:
Waters SYNAPT G2-Si HDMS
ACQUITY M Class UPLC
LEAP H/D-X PAL robot
Solutions
Quench solution: 400 mM potassium phosphate, 6 M guanidine hydrochloride, 0.5 M TCEP pH 2.5 (after 1:1 mixing with sample-quench solution pH-adjusted with NaOH to give this pH on mixing). Dilution buffer: 50 mM sodium phosphate 100 mM sodium chloride in water, pH 7.0.
Proteins
"CR2"=Human CR2 antigen (21-153), untagged; 135 uM in PBS.
"1053"=mAb; 80.7 uM in PBS.
HDX
For initial testing, CR2 was tested in a single run to check for digestion quality and signal strength. Protein was diluted to 10 uM in dilution buffer and run using a standard 1:20 dilution and quench protocol.
Searches using PLGS against a database of the CR2 mAb constructs used and pepsin sequences showed that the protein gave signals sufficient for excellent protein coverage. The CR2 sample was re-run a further two times under similar conditions to obtain triplicate digest data for peptide identification.

For the HDX experiment, the following two samples were prepared:
Apo (control sample): 7.4 ul CR2, 10 ul PBS, pH 7.4 (to match mAb buffer), 82.6 ul dilution buffer. +mAb: 7.4 ul CR2, 10 ul mAb 1053, 82.6 ul dilution buffer (giving 10 uM CR2, 8 uM mAb).
HPLC solvent A was 0.2% formic acid+0.03% TFA in water, solvent B was acetonitrile+0.2% formic acid. All chromatography steps were performed at 0° C.
Each protein was diluted 20-fold in deuterated dilution buffer stored at ambient temperature (25° C.), using incubation times of 0, 30 and 300 s and at 20° C. (zero time points were diluted in non-deuterated buffer). Following incubation, samples were quenched with 1 volume of quench solution at 0° C. After 1 min, the sample was injected onto an immobilised pepsin digestion column held at 15° C. and equilibrated in HPLC buffer A (Waters ENZYMATE BEH, 2.1 mm×30 mm, Part no: 186007233), with eluting peptides trapped onto a C18 guard column (2.1×5 mm Waters VANGUARD BEH C18 1.8 um 130 Å guard column, Part no 186003975) kept at 0° C. using a 4 min trap time. The trapped peptides were then eluted at a flow rate of 40 ul/min from the guard column onto an analytical C18 column (1.0×100 mm UPLC BEH C18, Part no 186002346), also at 0° C., and were separated using increasing concentrations of solvent B per the following gradient:

| Time (min) | % solvent B |
|---|---|
| 0.00 | 12 |
| 8.00 | 36 |
| 9.00 | 95 |
| 10.00 | 95 |
| 10.50 | 12 |
| 11.50 | 95 |
| 13.00 | 95 |
| 13.50 | 12 |
| 15.00 | 12 |

During this phase the pepsin column was offline and was washed with 2×100 ul injections of 2 M guanidine hydrochloride, 0.8% formic acid, 5% acetonitrile, 5% propan-2-ol, pH 2.5.
Eluted peptides were introduced into a Waters SYNAPT G2-Si mass spectrometer with electrospray source, and secondary lockspray introducing [Glu1]-fibrinopeptide B in 0.2% formic acid, 50% acetonitrile for internal mass calibration. Continuum data were acquired using "resolution" mode using positive ionisation over the m/z range 260 to 2000. For initial peptide identification samples, an MS$^e$ acquisition was used, where scans were acquired alternately in low energy and high energy collision cell conditions to generate intact and fragmented peptide data respectively. Deuteration samples were replicated five times (for 30 s and 300 s time-points) or twice (for zero deuteration samples) to increase the reliability of the data.
The initial CR2 characterisation data for MS$^e$ were used to generate peptide search lists using ProteinLynx Global Server (v3.0.2), searching against a database containing the sequence of the CR2 construct used. These peptide lists were used, with filtering to remove peptides identified with low confidence, to identify peptides and their degree of deuteration in samples from all time points in DynamX v3.0. Peptide and ion assignments were manually checked and refined where necessary.
Peptide-level differential (Apo-mAb complex) deuteration data were replotted in TIBCO SPOTFIRE v.7.0 (from the state data), see FIGS. 2A and 2B.

Results

Two closely related peptides showed consistently lower deuteration levels in the presence of mAb 1053:

```
(residues 66-96 of construct used, SEQ ID NO: 58)
FNKYSSCPEPIVPGGYKIRGSTPYRHGDSVT (residues 66-97 of construct used,SEQ ID NO: 59)
FNKYSSCPEPIVPGGYKIRGSTPYRHGDSVTF
```

The longer of these peptides showed higher error in the calculation of deuteration due to interference from overlapping ions, while the shorter of these peptides showed much cleaner data, such that the difference in deuteration between apo and mAb 1053 samples is statistically significant. The peptide SSCPEPIVPGGYKIRGSTPYRHGDSVT (residues 70-96 of construct used, SEQ ID NO: 60) differed only in missing the first 4 residues and showed a near absence of differential signal. The most likely reason for this difference is that the mAb-induced protection is mainly localised to the N-terminal 5 amides of peptide [66-96]. Residues 66-70 (sequence FNKYS, SEQ ID NO: 2) correspond to the linker between the two SCR domains. This region is the most likely candidate for the epitope of the mAb 1053.

In addition to these peptide differences, there was a further region showing lower protection (but for shorter peptides) near the C-terminus corresponding to peptides spanning residues 104-127 (SMNG-NKSVWCQANNMWGPTRLPTC, SEQ ID NO:71).

Impact of mAb 1053 on C3d/g-Opsonised Ligand Binding on B Cells

Example 2: Assay to Determine the Effect of mAb 1053 on C3dg Ligand Binding

This experiment determined the ability of mAb 1053 to prevent binding of C3dg:Streptavidin-APC complexes to non-cognate B cells. Fluorescently-labelled complexes of streptavidin and biotin-C3dg (recombinant) were incubated with human PBMCs and complex binding was assessed by flow cytometry.

Procedure

Fluorescently labelled tetramers of C3dg were generated using biotinylated C3dg and Streptavidin-APC. Complexes were generated by incubating biotinylated C3dg with Streptavidin-APC at a 4:1 ratio.

PBMCs were isolated from whole human blood by density gradient centrifugation. PBMCs were incubated with the indicated concentrations of CHO-expressed mAb 1053, isotype control antibody or no antibody, for 30 minutes at 37° C., 5% $CO_2$ in a humidified atmosphere. PBMCs were then incubated with C3dg:Streptavidin-APC complexes for a further 30 minutes.

The cells were fixed to preserve the ligand on the surface through subsequent staining. Fixed cells were incubated with anti-CD20-PE to identify B cells within the PBMC population. Stained PBMCs were fixed prior to quantification of ligand binding (APC fluorescence) on CD20+B cells by flow cytometry.

Results

Pre-incubation with mAb 1053 prevented complex binding in a dose-dependent manner with an $IC_{50}$ of 11.9 pM (N=4 donors, 2 independent experiments, mean normalised MFI±SEM, single curve fit to mean data and single $IC_{50}$ determined), whereas an isotype control antibody had no effect (see FIG. 4).

These data demonstrate that mAb 1053 can prevent binding of C3d/g-opsonised antigens to B cells, thereby impeding their CR2-dependent trafficking to FDCs.

Example 3: Affinities of Anti-CR2 Antibodies to Human and Cynomolgus Macaque CR2 at 25° C.

Procedure

Binding to recombinant soluble human and cynomolgus macaque (cyno) CR2 was assessed using the BIACORE T200 (GE Healthcare) surface plasmon resonance instrument. Protein A was immobilised on a CM5 biosensor chip by primary amine coupling. Test antibodies (HEK-expressed) were diluted to 5 µg/mL and captured on the Protein A surface for 120 seconds, followed by a 60 second dissociation time at 10 µL/minute. Capture time to achieve 267 RU were calculated using the binding stability report point with each antibody against each flow cell. Human and cyno CR2 antigen were titrated from a top concentration of 22 nM, over 8-points, 1 in 3 serial dilutions and passed over the captured antibodies for 600 seconds with a flow rate of 3 µL/minute. A 0 nM (i.e. buffer alone) injection was used to double reference the binding curves. The Protein A surface was regenerated using two 30 second injections of 50 mM sodium hydroxide between each cycle of CR2 titration. The run was carried out at 25° C. using HBS-EP as the running buffer. Data was analysed by setting a global R-max and using the equilibrium model inherent to the BIACORE analysis software for calculation of KD values. The results are shown in Table 3.

TABLE 3

| Affinities of HEK-expressed anti-CR2 antibodies to human and cyno CR2 | | |
|---|---|---|
| Antibody | KD to Human CR2 (nM) | KD to Cyno CR2 (nM) |
| 1053 | 0.257 | 0.287 |
| 996 | 0.301 | 0.430 |
| 999 | 0.319 | 0.437 |

Example 4: Assay to Determine the Effect of mAb 1053 on Serum-Opsonised PnPS14 Binding This experiment determined the ability of mAb 1053 to prevent binding of 'naturally-opsonised' ligand to non-cognate B cells. The ligand used was Pneumococcal Polysaccharide type 14 (PnPS14; a polysaccharide antigen expressed by *Streptococcus pneumoniae*) opsonised with normal human serum. Opsonised PnPS14 was incubated with human PBMCs, and binding was assessed by flow cytometry.

Procedure

PnPS14 was incubated in 100% NHS at 37° C. for 1 hour resulting in covalent deposition of opsonic C3 fragments, including C3dg.

PBMCs were isolated from whole human blood by density gradient centrifugation. PBMCs were incubated with the indicated concentrations of CHO-expressed mAb 1053, isotype control antibody or no antibody for 30 minutes at 37° C., 5% $CO_2$ in a humidified atmosphere. PBMCs were then incubated with serum-opsonised PnPS14 for a further 30 minutes.

The cells were fixed to preserve the ligand on the surface through subsequent staining. Fixed cells were incubated with anti-CD20-PE to identify B cells within the PBMC population. Bound PnPS14 was detected with PnPS14 anti-serum and subsequent staining with anti-rabbit IgG-FITC. Stained PBMCs were fixed prior to quantification of ligand binding (FITC fluorescence) on CD20+B cells by flow cytometry.

Results

Pre-incubation with mAb 1053 prevented binding of serum-opsonised PnPS14 to non-cognate B cells in a con-centration-dependent manner, with an $IC_{50}$ of 37.9 pM (N=4 donors, 2 independent experiments, mean normalised MFI±SEM, single curve fit to mean data and single $IC_{50}$ determined), whereas the isotype control antibody did not prevent binding (see FIG. 5).

These data demonstrate that mAb 1053 can prevent binding of C3d/g-opsonised antigens to B cells, thereby impeding their CR2-dependent trafficking to FDCs.

Example 5: Assay to Determine the Effect of mAb 1053 on Pre-Bound C3dg Ligand Binding This experiment determined if mAb 1053 could compete pre-bound ligand from non-cognate B cells, as a model of autoantigen displacement. Fluorescent streptavidin:C3dg-complexes were incubated with PBMCs and unbound ligand was washed away. mAb 1053 or isotype control antibody were added to the cells, and the amount of bound ligand was followed over time by flow cytometry.

Procedure

Fluorescently labelled tetramers of C3dg were generated using biotinylated C3dg and Streptavidin-APC. Complexes were generated by incubating biotinylated C3dg with Streptavidin-APC at a 4:1 ratio.

PBMCs were isolated from whole human blood by den-sity gradient centrifugation. PBMCs were incubated with C3dg:Streptavidin-APC complexes for 30 minutes at 37° C., 5% $CO_2$ in a humidified atmosphere. Unbound C3dg: Streptavidin-APC complexes were washed away. PBMCs were then incubated with 10 nM CHO-expressed mAb 1053, isotype control antibody or no antibody for 0.5, 2 or 18.5 hours.

The cells were fixed to preserve the ligand on the surface through subsequent staining. Fixed cells were incubated with anti-CD20-PE to identify B cells within the PBMC population. Stained PBMCs were fixed prior to quantifica-tion of ligand binding (APC fluorescence) on CD20+ B cells by flow cytometry.

Results mAb 1053 rapidly competed off pre-bound C3dg:Strepta-vidin-APC complexes from non-cognate B cells, whereas an isotype control antibody had no effect. The majority of this effect had occurred within 2 hours of addition. The isotype control antibody did not reduce binding compared to the no antibody (N=4 donors, 2 independent experiments, mean normalised MFI±SEM) (see FIG. 6).

These data demonstrate that mAb 1053 can rapidly and potently compete pre-bound C3dg-opsonised antigens from CR2-expressing cells.

Examples 6 to 9: Impact of mAb 1053 on B Cell Activation

Co-ligation of CR2 with an antigen-specific BCR by C3d/g-opsonised antigens lowers the threshold for B cell activation. To model this with non-cognate B cells, multi-meric complexes were generated to act as surrogates for C3dg-opsonised antigens. Biotinylated anti-BCR reagents (recognising either the λ chain or IgM) were used to mimic antigen interaction with the BCR, and biotinylated recom-binant C3dg was used as the CR2 ligand. These components were co-incubated with Neutravidin, resulting in complexes containing both anti-BCR and C3dg; anti-BCR:C3dg com-plex.

As the major role of CR2 in the system is to lower the threshold for BCR activation, assays were optimised by titration of the anti-BCR reagent to levels that induced little or no signal. Upon the inclusion of C3dg in the complexes, co-ligation of CR2 lowered the threshold for B cell activa-tion, resulting in a C3dg-dependent window of activation.

Example 6: Assay to Determine the Effect of mAb 1053 on Calcium Flux and Phosphoprotein Signalling in Primary Human B Cells To assess the ability of mAb 1053 to block the signalling events downstream of CR2-dependent BCR activation, intracellular calcium flux was monitored in B cells by flow cytometry after stimulation of PBMCs with the anti-BCR: C3dg Complex.

Procedure

PBMCs were isolated from whole human blood by den-sity gradient centrifugation. PBMCs were loaded with the calcium responsive dye Fluo-4 and B cells were identified with anti-CD19 BV421. Fluo-4 fluorescence at baseline and after stimulation was monitored in real time by flow cytom-etry. Cells were stimulated with anti-BCR:C3dg complexes to elicit CR2-dependent release of intracellular calcium downstream of the BCR. Stimulation was performed after pre-incubation for 30 minutes at room temperature with the indicated concentrations of CHO-expressed mAb 1053. The time of peak C3dg-dependent response in the absence of mAb 1053 was extrapolated to yield equivalent response values at that time point in samples containing mAb 1053. Responses were normalised such that the maximum response in each dataset=100%. N=4 individuals, mean±SD.

Results

A dose-dependent decrease in the calcium flux signal was seen with mAb 1053, resulting in an $IC_{50}$ of 9.0 pM (see FIG. 7).

These data demonstrate that mAb 1053 can potently inhibit calcium signalling immediately downstream of BCR activation in primary human B cells.

Example 7: Assay to Determine the Effect of mAb 1053 on Phospho-Protein Signalling in Primary Human B Cells To assess the ability of mAb 1053 to block the signalling events downstream of CR2-dependent BCR activation, the levels of phosphorylated ERK1/2 (PERK) and phosphory-lated AKT (pAKT) were measured in B cells by intracellular flow cytometry after stimulation of PBMCs with the anti-BCR:C3dg complex.

Procedure

PBMCs were isolated from whole human blood by den-sity gradient centrifugation and incubated for 2 hours at 37° C., 5% $CO_2$ in a humidified atmosphere. PBMCs were then pre-incubated with the indicated concentrations of CHO-expressed mAb 1053 for 30 minutes. Cells were stimulated for 10 minutes at 37° C. with the anti-BCR:C3dg complex, stopped by fixation, permeabilized and stored at −20° C. overnight. Cells were stained with anti-CD20-PE to identify B cells, anti-pAKT (pS473)-ALEXA 647 and anti-pERK-ALEXA 488. Fluorescence was assessed by flow cytometry and normalised % pERK+ and pAKT+ values were determined in CD20+ cells. N=4 individuals, mean±SD.

Results

Titration of mAb 1053 levels resulted in strong inhibition of the pERK response with an $IC_{50}$ of 2.7 nM (FIG. 8a). Assessment of the Complex-stimulated phospho-AKT signal in the same PBMC assay gave an $IC_{50}$ for mAb 1053 of 3.8 nM (FIG. 8b). Together, these data demonstrate the ability of mAb 1053 to prevent signalling in primary human B cells following stimulation with the model CR2/BCR ligand complex.

mAb 1053 strongly inhibited the pERK response in a dose-dependent manner with an $IC_{50}$ of 2.7 nM (see FIG. 8a). pAKT signalling was similarly inhibited by mAb 1053, with an $IC_{50}$ of 3.8 nM (see FIG. 8b).

These data demonstrate the ability of mAb 1053 to prevent phospho-protein signalling downstream of BCR activation in primary human B cells.

Example 8: Assay to Determine the Effect of mAb 1053 on Primary Human B Cell Activation as Determined by CD69 Upregulation To assess the ability of mAb 1053 to block the signalling events downstream of CR2-dependent BCR activation, cell surface expression of CD69 (an activation marker) was measured in primary human B cells by flow cytometry after stimulation of PBMCs with the anti-BCR:C3dg complex.

Procedure

Frozen PBMCs (isolated from whole human blood by density gradient centrifugation) from combined donors were thawed and incubated with the indicated concentrations of HEK-expressed mAb 1053 or isotype control antibody for 30 minutes at 37° C., 5% CO2 in a humidified atmosphere. Cells were stimulated with the anti-BCR:C3dg complex and incubated for a further 4 hours, followed by fixation. Cells were stained with anti-CD20-A647 to identify B cells, and anti-CD69-PE. Fluorescence was assessed by flow cytometry and normalised % CD69 response was determined in CD20+ cells. N=4 independent assessments, mean±SD.

Results mAb 1053 potently inhibited CD69 upregulation with an $IC_{50}$ of 4.4 nM, whereas the isotype control antibody did not (see FIG. 9).

These data demonstrate the ability of mAb 1053 to prevent upregulation of cell surface CD69 downstream of BCR activation in primary human B cells.

Example 9: Assay to Determine the Effects of mAb 996, mAb 999 and mAb 1053 on Antibody Secretion in Primary Human B Cells To assess the ability of mAb 1053 to block functional responses in primary human B cells, secreted immunoglobulin levels were measured in primary human B cells by MSD after stimulation of B cells with the anti-BCR:C3dg complex.

Procedure

B cells were isolated from previously frozen PBMCs from a single donor (isolated from whole human blood by density gradient centrifugation) by negative magnetic separation removing non-B cells and plasma cells. Cells were pre-incubated in culture medium with 5 μg/ml HEK-expressed mAb 996, mAb 999, mAb 1053, isotype control antibody, or with no mAb for 30 minutes at 37° C., 5% CO2 in a humidified atmosphere. B cells were stimulated with the anti-BCR:C3dg complex, or with complex containing no C3dg ('no C3dg' control). The culture medium contained sub-optimal concentrations of IL-21 and CD40L, to maintain cell survival. After four days, cell supernatants were harvested and assayed for IgA using an MSD assay kit. The IgA concentrations were calculated from the standard curve and the median fold increase over the 'no C3dg' control was calculated as the CR2-dependent window of activation. N=11 donors, mean±SE.

Results mAb 996, mAb 999, and mAb 1053 potently inhibited C3dg-dependent IgA secretion from primary human B cells, whereas the isotype control antibody did not (see FIG. 10).

These data demonstrate the ability of mAb 996, mAb 999, and mAb 1053 to prevent the C3dg-dependent functional output of immunoglobulin secretion in primary human B cells.

Examples 10 and 11: Impact of mAb 1053 on Primary Human Follicular Dendritic Cells (FDCs)

A critical role for the FDC in autoimmunity is the CR2-dependent binding to, and retention of, C3d/g-opsonised antigens for persistent presentation to cognate B cells in the GC/ELS.

Example 10: Assay to Determine Target Engagement of mAb 1053 on Primary Human FDCs This experiment determined the on-cell binding affinity of mAb 1053 on primary human FDCs. Unlabelled mAb 1053 was titrated onto FDC-enriched human tonsil digests followed by an excess of fluorescently-labelled mAb 1053. FDCs were identified and antibody binding was assessed by flow cytometry.

Procedure

Human tonsils from a single donor were mechanically disrupted and enzymatically digested to liberate FDCs and the digests were CD45-depleted by negative magnetic separation. The CD45-depleted tonsil digests were pre-incubated for 20 minutes at room temperature with the indicated concentrations of unlabelled CHO-expressed mAb 1053. Cells were then incubated with antibodies to identify FDCs by flow cytometry, and a saturating concentration of PE-labelled mAb 1053 (mAb 1053-PE, 1 g/ml) for 30 minutes. Lineage+ cells were identified with antibodies recognising CD11b, CD45, CD31 and CD34. Cells were gated to identify FDCs (lineage– gp38+CD21+ (using a non-competitive clone, Bu32)). The geomean of uninhibited mAb 1053-PE staining was set at 100%. Data are mean±SE of 4 individual donors.

Results

Target engagement of mAb 1053 on FDCs was concentration-dependent with an $EC_{50}$ calculated from the on-cell binding curve of 62.2 pM (see FIG. 11).

These data demonstrate that mAb 1053 engages the CR2 target with high affinity on primary human FDCs.

Example 11: Assay to Determine the Effect of mAb 1053 on C3dg Ligand Binding on Primary Human FDCs This experiment determined the ability of mAb 1053 to prevent binding of C3dg ligand complexes to human FDCs. Fluorescently-labelled complexes of streptavidin and biotin- C3dg (recombinant) were incubated with human tonsil digests, and complex binding was assessed by flow cytometry.

Procedure

Fluorescently labelled tetramers of C3dg were generated using biotinylated C3dg and Streptavidin-APC. Complexes were generated by incubating biotinylated C3dg with Streptavidin-APC at a 4:1 ratio.

Human tonsils from a single donor were mechanically disrupted and enzymatically digested to liberate FDCs and the digests were CD45-depleted by negative magnetic separation. The CD45-depleted tonsil digests were pre-incubated for 20 minutes at room temperature with the indicated concentrations of unlabelled CHO-expressed mAb 1053. Cells were then incubated with antibodies to identify FDCs by flow cytometry, and 10 µg/ml C3dg:streptavidin-APC ligand complex, for 30 minutes. Lineage+ cells were identified with antibodies recognising CD11b, CD45, CD31 and CD34. Cells were gated to identify FDCs (lineage– gp38+ CD21+ (using a non-competitive clone, Bu32)). The geomean of C3dg (APC) staining was set at 100%. Data are mean±SE of 4 individual donors.

Results

Pre-incubation of the tonsil digests with mAb 1053 prevented ligand binding in a dose-dependent manner with an $IC_{50}$ of 47.0 pM (see FIG. 12).

These data demonstrate that mAb 1053 can potently inhibit binding of C3dg-ligand to primary human FDCs, thereby impeding retention of complement-opsonised antigens.

---

BIOLOGICAL DATA
SEQUENCES

---

SEQ ID NO: 1: Human CR2 sequence
ISCGSPPPILNGRISYYSTPIAVGTVIRYSCSGTFRLIGEKSLLCITKDKVDGTWDKPAPKC

EYFNKYSSCPEPIVPGGYKIRGSTPYRHGDSVTFACKTNFSMNGNKSVWCQANNMWGP

TRLPTCVSVFPLECPALPMIHNGHHTSENVGSIAPGLSVTYSCESGYLLVGEKIINCLSSG

KWSAVPPTCEEARCKSLGRFPNGKVKEPPILRVGVTANFFCDEGYRLQGPPSSRCVIAGQ

GVAWTKMPVCEEIFCPSPPPILNGRHIGNSLANVSYGSIVTYTCDPDPEEGVNFILIGESTL

RCTVDSQKTGTWSGPAPRCELSTSAVQCPHPQILRGRMVSGQKDRYTYNDTVIFACMF

GFTLKGSKQIRCNAQGTWEPSAPVCEKECQAPPNILNGQKEDRHMVRFDPGTSIKYSCN

PGYVLVGEESIQCTSEGVWTPPVPQCKVAACEATGRQLLTKPQHQFVRPDVNSSCGEGY

KLSGSVYQECQGTIPWFMEIRLCKEITCPPPPVIYNGAHTGSSLEDFPYGTTVTYTCNPGP

ERGVEFSLIGESTIRCTSNDQERGTWSGPAPLCKLSLLAVQCSHVHIANGYKISGKEAPYF

YNDTVTFKCYSGFTLKGSSQIRCKADNTWDPEIPVCEKETCQHVRQSLQELPAGSRVEL

VNTSCQDGYQLTGHAYQMCQDAENGIWFKKIPLCKVIHCHPPPVIVNGKHTGMMAENF

LYGNEVSYECDQGFYLLGEKKLQCRSDSKGHGSWSGPSPQCLRSPPVTRCPNPEVKHG

YKLNKTHSAYSHNDIVYVDCNPGFIMNGSRVIRCHTDNTWVPGVPTCIKKAFIGCPPPPK

TPNGNHTGGNIARFSPGMSILYSCDQGYLLVGEALLLCTHEGTWSQPAPHCKEVNCSSP

ADMDGIQKGLEPRKMYQYGAVVTLECEDGYMLEGSPQSQCQSDHQWNPPLAVCRSRS

LAPVLCGIAAGLILLTFLIVITLYVISKHRARNYYTDTSQKEAFHLEAREVYSVDPYNPAS

SEQ ID NO: 2: Human CR2 epitope
FNKYS

SEQ ID NO: 3: Amino acid sequence of 1053 heavy chain
QLQLQESGPGLVKPSETLSLTCTVSGGSISSDSYYWGWIRQPPGKGLEWIGSIHYSGSTY

YNPPLESRVTISVDTSKNQFSLKLSSVTAADTAVYYCAREGGPRHGWSWGQGTLVTVSS

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELAGA

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

-continued

BIOLOGICAL DATA
SEQUENCES

SEQ ID NO: 4: Amino acid sequence of 1053 light chain
DIQMTQSPSSLSASVGDRVTITCQASQDISEYLNWYQQKPGKAPKLLIYDASNLETGVPS

RFSGSGSGTDFTFTISSLQPEDIATYYCQQDSNLPITFGGGTKVEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC

SEQ ID NO: 5: Amino acid sequence of 1053 variable heavy
chain
QLQLQESGPGLVKPSETLSLTCTVSGGSISSDSYYWGWIRQPPGKGLEWIGSIHYSGSTY

YNPPLESRVTISVDTSKNQFSLKLSSVTAADTAVYYCAREGGPRHGWSWGQGTLVTVSS

SEQ ID NO: 6: Amino acid sequence of 1053 variable light
chain
DIQMTQSPSSLSASVGDRVTITCQASQDISEYLNWYQQKPGKAPKLLIYDASNLETGVPS

RFSGSGSGTDFTFTISSLQPEDIATYYCQQDSNLPITFGGGTKVEIK

SEQ ID NO: 7: Amino acid sequence of 1053 CDRH1
SDSYYWG

SEQ ID NO: 8: Amino acid sequence of 1053 CDRH2
SIHYSGSTYYNPPLES

SEQ ID NO: 9: Amino acid sequence of 1053 CDRH3
EGGPRHGWS

SEQ ID NO: 10: Amino acid sequence of 1053 CDRL1
QASQDISEYLN

SEQ ID NO: 11: Amino acid sequence of 1053 CDRL2
DASNLET

SEQ ID NO: 12: Amino acid sequence of 1053 CDRL3
QQDSNLPIT

SEQ ID NO: 13: Nucleic acid sequence encoding 1053
heavy chain
CAGCTCCAGCTGCAGGAGAGCGGCCCCAGGCCTGGTGAAACCCAGCGAGACCCTGAG

CCTGACCTGCACCGTGAGCGGAGGCAGCATCAGCTCCGACAGCTACTACTGGGGCT

GGATTAGGCAGCCTCCCGGCAAGGGCCTGGAGTGGATCGGAAGCATCCACTACAGC

GGCAGCACCTACTACAACCCACCCCTGGAGAGCAGGGTGACCATCAGCGTGGACAC

CAGCAAGAACCAGTTCAGCCTGAAGCTGAGCAGCGTCACAGCAGCCGACACCGCCG

TGTACTATTGCGCCAGGGAGGGCGGACCCAGGCACGGCTGGAGCTGGGGCCAGGGC

ACCCTGGTGACCGTGAGCAGCGCAAGCACCAAGGGCCCCAGCGTGTTCCCCCTGGC

CCCCAGCAGCAAGAGCACCAGCGGCGGCACAGCCGCCCTGGGCTGCCTGGTGAAGG

ACTACTTCCCCGAGCCCGTGACCGTGTCCTGGAACAGCGGAGCCCTGACCAGCGGC

GTGCACACCTTCCCCGCCGTGCTGCAGAGCAGCGGCCTGTACAGCCTGAGCAGCGT

GGTGACCGTGCCCAGCAGCAGCCTGGGCACCCAGACCTACATCTGTAACGTGAACC

ACAAGCCCAGCAACACCAAGGTGGACAAGAAGGTGGAGCCCAAGAGCTGTGACAA

GACCCACACCTGCCCCCCCTGCCCCTGCCCCCGAGCTGgccGGAGcCCCCAGCGTGTTC

CTGTTCCCCCCCAAGCCTAAGGACACCCTGATGATCAGCAGAACCCCCGAGGTGAC

CTGTGTGGTGGTGGATGTGAGCCACGAGGACCCTGAGGTGAAGTTCAACTGGTACG

TGGACGGCGTGGAGGTGCACAATGCCAAGACCAAGCCCAGGGAGGAGCAGTACAA

CAGCACCTACCGGGTGGTGTCCGTGCTGACCGTGCTGCACCAGGATTGGCTGAACG

BIOLOGICAL DATA
SEQUENCES

GCAAGGAGTACAAGTGTAAGGTGTCCAACAAGGCCCTGCCTGCCCCTATCGAGAAA

ACCATCAGCAAGGCCAAGGGCCAGCCCAGAGAGCCCCAGGTGTACACCCTGCCCCC

TAGCAGAGATGAGCTGACCAAGAACCAGGTGTCCCTGACCTGCCTGGTGAAGGGCT

TCTACCCCAGCGACATCGCCGTGGAGTGGGAGAGCAACGGCCAGCCCGAGAACAAC

TACAAGACCACCCCCCCTGTGCTGGACAGCGATGGCAGCTTCTTCCTGTACAGCAAG

CTGACCGTGGACAAGAGCAGATGGCAGCAGGGCAACGTGTTCAGCTGCTCCGTGAT

GCACGAGGCCCTGCACAATCACTACACCCAGAAGAGCCTGAGCCTGTCCCCTGGCA

AG

SEQ ID NO: 14: Nucleic acid sequence encoding 1053
light chain
GACATCCAGATGACTCAGTCCCCCTCTAGCCTGAGCGCTAGCGTGGGCGACAGGGT

GACCATCACCTGCCAGGCCAGCCAGGACATCAGCGAGTACCTGAACTGGTACCAGC

AGAAGCCCGGCAAGGCCCCCAAACTGCTGATCTACGACGCCTCAAACCTCGAGACC

GGCGTGCCTAGCAGGTTTAGCGGCAGCGGCAGCGGCACCGACTTCACCTTCACCATC

AGCAGCCTGCAGCCCGAGGATATCGCCACCTACTACTGCCAGCAGGACAGCAACCT

GCCCATCACCTTCGGCGGAGGCACCAAGGTGGAGATTAAGCGTACGGTGGCCGCCC

CCAGCGTGTTCATCTTCCCCCCCAGCGATGAGCAGCTGAAGAGCGGCACCGCCAGC

GTGGTGTGTCTGCTGAACAACTTCTACCCCCGGGAGGCCAAGGTGCAGTGGAAGGT

GGACAATGCCCTGCAGAGCGGCAACAGCCAGGAGAGCGTGACCGAGCAGGACAGC

AAGGACTCCACCTACAGCCTGAGCAGCACCCTGACCCTGAGCAAGGCCGACTACGA

GAAGCACAAGGTGTACGCCTGTGAGGTGACCCACCAGGGCCTGTCCAGCCCCGTGA

CCAAGAGCTTCAACCGGGGCGAGTGC

SEQ ID NO: 15: Amino acid sequence of 996 heavy chain
QLQLQESGPGLVKPSETLSLTCTVSGGSISSSSYYWGWIRQPPGKGLEWIGSIHNSGSTYY

NPPLKSRVTISVDTSKNQFSLKLSSVTAADTAVYYCAREGGPRHGWSWGQGTLVTVSS

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELAGA

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

SEQ ID NO: 16: Amino acid sequence of 996 light chain
DIQMTQSPSSLSASVGDRVTITCQASQDISTFLNWYQQKPGKAPKLLIYDASNLETGVPS

RFSGSGSGTDFTFTISSLQPEDIATYYCQQDSILPITFGGGTKVEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC

SEQ ID NO: 17: Amino acid sequence of 996 variable heavy
chain
QLQLQESGPGLVKPSETLSLTCTVSGGSISSSSYYWGWIRQPPGKGLEWIGSIHNSGSTY

YNPPLKSRVTISVDTSKNQFSLKLSSVTAADTAVYYCAREGGPRHGWSWGQGTLVTVS

S

-continued

```
                        BIOLOGICAL DATA
                          SEQUENCES
```

SEQ ID NO: 18: Amino acid sequence of 996 variable light
chain
DIQMTQSPSSLSASVGDRVTITCQASQDISTFLNWYQQKPGKAPKLLIYDASNLETGVPS

RFSGSGSGTDFTFTISSLQPEDIATYYCQQDSILPITFGGGTKVEIK

SEQ ID NO: 19: Amino acid sequence of 996 CDRH1
SSSYYWG

SEQ ID NO: 20: Amino acid sequence of 996 CDRH2
SIHNSGSTYYNPPLKS

SEQ ID NO: 21: Amino acid sequence of 996 CDRH3
EGGPRHGWS

SEQ ID NO: 22: Amino acid sequence of 996 CDRL1
QASQDISTFLN

SEQ ID NO: 23: Amino acid sequence of 996 CDRL2
DASNLET

SEQ ID NO: 24: Amino acid sequence of 996 CDRL3
QQDSILPIT

SEQ ID NO: 25: Nucleic acid sequence encoding 996 heavy
chain
CAGCTCCAGCTGCAGGAGAGCGGCCCAGGCCTGGTGAAACCCAGCGAGACCCTGAG

CCTGACCTGCACCGTGAGCGGAGGCAGCATCAGCTCCAGCAGCTACTACTGGGGCT

GGATTAGGCAGCCTCCCGGCAAGGGCCTGGAGTGGATCGGAAGCATCCACAACAGC

GGCAGCACCTACTACAACCCACCCCTGAAGAGCAGGGTGACCATCAGCGTGGACAC

CAGCAAGAACCAGTTCAGCCTGAAGCTGAGCAGCGTCACAGCAGCCGACACCGCCG

TGTACTATTGCGCCAGGGAGGGCGGACCCAGGCACGGCTGGAGCTGGGGCCAGGGC

ACCCTGGTGACCGTGAGCAGCGCAAGCACCAAGGGCCCCAGCGTGTTCCCCCTGGC

CCCCAGCAGCAAGAGCACCAGCGGCGGCACAGCCGCCCTGGGCTGCCTGGTGAAGG

ACTACTTCCCCGAGCCCGTGACCGTGTCCTGGAACAGCGGAGCCCTGACCAGCGGC

GTGCACACCTTCCCCGCCGTGCTGCAGAGCAGCGGCCTGTACAGCCTGAGCAGCGT

GGTGACCGTGCCCAGCAGCAGCCTGGGCACCCAGACCTACATCTGTAACGTGAACC

ACAAGCCCAGCAACACCAAGGTGGACAAGAAGGTGGAGCCCAAGAGCTGTGACAA

GACCCACACCTGCCCCCCCTGCCCTGCCCCCGAGCTGgccGGAGcCCCCAGCGTGTTC

CTGTTCCCCCCCAAGCCTAAGGACACCCTGATGATCAGCAGAACCCCCGAGGTGAC

CTGTGTGGTGGTGGATGTGAGCCACGAGGACCCTGAGGTGAAGTTCAACTGGTACG

TGGACGGCGTGGAGGTGCACAATGCCAAGACCAAGCCCAGGGAGGAGCAGTACAA

CAGCACCTACCGGGTGGTGTCCGTGCTGACCGTGCTGCACCAGGATTGGCTGAACG

GCAAGGAGTACAAGTGTAAGGTGTCCAACAAGGCCCTGCCTGCCCCTATCGAGAAA

ACCATCAGCAAGGCCAAGGGCCAGCCCAGAGAGCCCCAGGTGTACACCCTGCCCCC

TAGCAGAGATGAGCTGACCAAGAACCAGGTGTCCCTGACCTGCCTGGTGAAGGGCT

TCTACCCCAGCGACATCGCCGTGGAGTGGGAGAGCAACGGCCAGCCCGAGAACAAC

TACAAGACCACCCCCCCTGTGCTGGACAGCGATGGCAGCTTCTTCCTGTACAGCAAG

CTGACCGTGGACAAGAGCAGATGGCAGCAGGGCAACGTGTTCAGCTGCTCCGTGAT

GCACGAGGCCCTGCACAATCACTACACCCAGAAGAGCCTGAGCCTGTCCCCTGGCA

AG
```

BIOLOGICAL DATA
SEQUENCES

SEQ ID NO: 26: Nucleic acid sequence encoding 996 light
chain
GACATCCAGATGACTCAGTCCCCCTCTAGCCTGAGCGCTAGCGTGGGCGACAGGGT

GACCATCACCTGCCAGGCCAGCCAGGACATCAGCACCTTCCTGAACTGGTACCAGC

AGAAGCCCGGCAAGGCCCCCAAACTGCTGATCTACGACGCCTCAAACCTCGAGACC

GGCGTGCCTAGCAGGTTTAGCGGCAGCGGCAGCGGCACCGACTTCACCTTCACCATC

AGCAGCCTGCAGCCCGAGGATATCGCCACCTACTACTGCCAGCAGGACAGCATCCT

GCCCATCACCTTCGGCGGAGGCACCAAGGTGGAGATTAAGCGTACGGTGGCCGCCC

CCAGCGTGTTCATCTTCCCCCCCAGCGATGAGCAGCTGAAGAGCGGCACCGCCAGC

GTGGTGTGTCTGCTGAACAACTTCTACCCCCGGGAGGCCAAGGTGCAGTGGAAGGT

GGACAATGCCCTGCAGAGCGGCAACAGCCAGGAGAGCGTGACCGAGCAGGACAGC

AAGGACTCCACCTACAGCCTGAGCAGCACCCTGACCCTGAGCAAGGCCGACTACGA

GAAGCACAAGGTGTACGCCTGTGAGGTGACCCACCAGGGCCTGTCCAGCCCCGTGA

CCAAGAGCTTCAACCGGGGCGAGTGC

SEQ ID NO: 27: Amino acid sequence of 999 heavy chain
QLQLQESGPGLVKPSETLSLTCTVSGGSISSSSYYWGWIRQPPGKGLEWIGSIHYSGSTYY

NPPLESRVTISVDTSKNQFSLKLSSVTAADTAVYYCAREGGPRHGWSWGQGTLVTVSSA

STKGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPPCPAPELAGAP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

SEQ ID NO: 28: Amino acid sequence of 999 light chain
DIQMTQSPSSLSASVGDRVTITCQASHDISNFLNWYQQKPGKAPKLLIYDTSNLETGVPS

RFSGSGSGTDFTFTISSLQPEDIATYYCQQDSILPITFGGGTKVEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC

SEQ ID NO: 29: Amino acid sequence of 999 variable heavy
chain
QLQLQESGPGLVKPSETLSLTCTVSGGSISSSSYYWGWIRQPPGKGLEWIGSIHYSGSTY

YNPPLESRVTISVDTSKNQFSLKLSSVTAADTAVYYCAREGGPRHGWSWGQGTLVTVSS

SEQ ID NO: 30: Amino acid sequence of 999 variable light
chain
DIQMTQSPSSLSASVGDRVTITCQASHDISNFLNWYQQKPGKAPKLLIYDTSNLETGVPS

RFSGSGSGTDFTFTISSLQPEDIATYYCQQDSILPITFGGGTKVEIK

SEQ ID NO: 31: Amino acid sequence of 999 CDRH1
SSSYYWG

SEQ ID NO: 32: Amino acid sequence of 999 CDRH2
SIHYSGSTYYNPPLES

SEQ ID NO: 33: Amino acid sequence of 999 CDRH3
EGGPRHGWS

SEQ ID NO: 34: Amino acid sequence of 999 CDRL1
QASHDISNFLN

-continued

BIOLOGICAL DATA
SEQUENCES

SEQ ID NO: 35: Amino acid sequence of 999 CDRL2
DTSNLET

SEQ ID NO: 36: Amino acid sequence of 999 CDRL3
QQDSILPIT

SEQ ID NO: 37: Nucleic acid sequence encoding 999 heavy
chain
CAGCTCCAGCTGCAGGAGAGCGGCCCAGGCCTGGTGAAACCCAGCGAGACCCTGAG

CCTGACCTGCACCGTGAGCGGAGGCAGCATCAGCTCCAGCAGCTACTACTGGGGCT

GGATTAGGCAGCCTCCCGGCAAGGGCCTGGAGTGGATCGGAAGCATCCACTACAGC

GGCAGCACCTACTACAACCCACCCCTGGAGAGCAGGGTGACCATCAGCGTGGACAC

CAGCAAGAACCAGTTCAGCCTGAAGCTGAGCAGCGTCACAGCAGCCGACACCGCCG

TGTACTATTGCGCCAGGGAGGGCGGACCCAGGCACGGCTGGAGCTGGGGCCAGGGC

ACCCTGGTGACCGTGAGCAGCGCAAGCACCAAGGGCCCCAGCGTGTTCCCCCTGGC

CCCCAGCAGCAAGAGCACCAGCGGCGGCACAGCCGCCCTGGGCTGCCTGGTGAAGG

ACTACTTCCCCGAGCCCGTGACCGTGTCCTGGAACAGCGGAGCCCTGACCAGCGGC

GTGCACACCTTCCCCGCCGTGCTGCAGAGCAGCGGCCTGTACAGCCTGAGCAGCGT

GGTGACCGTGCCCAGCAGCAGCCTGGGCACCCAGACCTACATCTGTAACGTGAACC

ACAAGCCCAGCAACACCAAGGTGGACAAGAAGGTGGAGCCCAAGAGCTGTGACAA

GACCCACACCTGCCCCCCCTGCCCTGCCCCCGAGCTGGCCGGAGCCCCCAGCGTGTT

CCTGTTCCCCCCCAAGCCTAAGGACACCCTGATGATCAGCAGAACCCCCGAGGTGA

CCTGTGTGGTGGTGGATGTGAGCCACGAGGACCCTGAGGTGAAGTTCAACTGGTAC

GTGGACGGCGTGGAGGTGCACAATGCCAAGACCAAGCCCAGGGAGGAGCAGTACA

ACAGCACCTACCGGGTGGTGTCCGTGCTGACCGTGCTGCACCAGGATTGGCTGAAC

GGCAAGGAGTACAAGTGTAAGGTGTCCAACAAGGCCCTGCCTGCCCCTATCGAGAA

AACCATCAGCAAGGCCAAGGGCCAGCCCAGAGAGCCCCAGGTGTACACCCTGCCCC

CTAGCAGAGATGAGCTGACCAAGAACCAGGTGTCCCTGACCTGCCTGGTGAAGGGC

TTCTACCCCAGCGACATCGCCGTGGAGTGGGAGAGCAACGGCCAGCCCGAGAACAA

CTACAAGACCACCCCCCCTGTGCTGGACAGCGATGGCAGCTTCTTCCTGTACAGCAA

GCTGACCGTGGACAAGAGCAGATGGCAGCAGGGCAACGTGTTCAGCTGCTCCGTGA

TGCACGAGGCCCTGCACAATCACTACACCCAGAAGAGCCTGAGCCTGTCCCCTGGC

AAG

SEQ ID NO: 38: Nucleic acid sequence encoding 999 light
chain
GACATCCAGATGACTCAGTCCCCCTCTAGCCTGAGCGCTAGCGTGGGCGACAGGGT

GACCATCACCTGCCAGGCCAGCCACGACATCAGCAACTTCCTGAACTGGTACCAGC

AGAAGCCCGGCAAGGCCCCCAAACTGCTGATCTACGACACCTCAAACCTCGAGACC

GGCGTGCCTAGCAGGTTTAGCGGCAGCGGCAGCGGCACCGACTTCACCTTCACCATC

AGCAGCCTGCAGCCCGAGGATATCGCCACCTACTACTGCCAGCAGGACAGCATCCT

GCCCATCACCTTCGGCGGAGGCACCAAGGTGGAGATTAAGCGTACGGTGGCCGCCC

CCAGCGTGTTCATCTTCCCCCCCAGCGATGAGCAGCTGAAGAGCGGCACCGCCAGC

GTGGTGTGTCTGCTGAACAACTTCTACCCCCGGGAGGCCAAGGTGCAGTGGAAGGT

-continued

BIOLOGICAL DATA
SEQUENCES

GGACAATGCCCTGCAGAGCGGCAACAGCCAGGAGAGCGTGACCGAGCAGGACAGC

AAGGACTCCACCTACAGCCTGAGCAGCACCCTGACCCTGAGCAAGGCCGACTACGA

GAAGCACAAGGTGTACGCCTGTGAGGTGACCCACCAGGGCCTGTCCAGCCCCGTGA

CCAAGAGCTTCAACCGGGGCGAGTGC

SEQ ID NO: 39:
MISCGSPPPIL

SEQ ID NO: 40:
MISCGSPPPILNGRISY

SEQ ID NO: 41:
YSTPIAVG

SEQ ID NO: 42:
YSTPIAVGT

SEQ ID NO: 43:
YSTPIAVGTVIRYSCSGT

SEQ ID NO: 44:
TVIRYSCSGT

SEQ ID NO: 45:
TVIRYSCSGTF

SEQ ID NO: 46:
VIRYSCSGT

SEQ ID NO: 47:
FRLIGEKS

SEQ ID NO: 48:
FRLIGEKSL

SEQ ID NO: 49:
FRLIGEKSLL

SEQ ID NO: 50:
RLIGEKSL

SEQ ID NO: 51:
RLIGEKSLL

SEQ ID NO: 52:
IGEKSLL

SEQ ID NO: 53:
GEKSLLCITKDKVDGTWDKPA

SEQ ID NO: 54:
CITKDKVDGT

SEQ ID NO: 55:
CITKDKVDGTWDKPAPKCEY

SEQ ID NO: 56:
KVDGTWDKPAPKCEY

SEQ ID NO: 57:
WDKPAPKCEY

SEQ ID NO: 58:
FNKYSSCPEPIVPGGYKIRGSTPYRHGDSVT

SEQ ID NO: 59:
FNKYSSCPEPIVPGGYKIRGSTPYRHGDSVTF

SEQ ID NO: 60:
SSCPEPIVPGGYKIRGSTPYRHGDSVT

SEQ ID NO: 61:
YKIRGSTPYRHGDSVT

-continued

BIOLOGICAL DATA
SEQUENCES

SEQ ID NO: 62:
YKIRGSTPYRHGDSVTF

SEQ ID NO: 63:
KIRGSTPYRHGDSVT

SEQ ID NO: 64:
KIRGSTPYRHGDSVTF

SEQ ID NO: 65:
FACKTNF

SEQ ID NO: 66:
SMNGNKSVW

SEQ ID NO: 67:
SMNGNKSVWC

SEQ ID NO: 68:
SMNGNKSVWCQA

SEQ ID NO: 69:
SMNGNKSVWCQANNM

SEQ ID NO: 70:
SMNGNKSVWCQANNMWGPTRL

SEQ ID NO: 71:
SMNGNKSVWCQANNMWGPTRLPTC

SEQ ID NO: 72:
NNMWGPTRL

SEQ ID NO: 73:
NNMWGPTRLPTCV

SEQ ID NO: 74:
VSVFPLE

SEQUENCE LISTING

<160> NUMBER OF SEQ ID NOS: 74

<210> SEQ ID NO 1
<211> LENGTH: 1013
<212> TYPE: PRT
<213> ORGANISM: Human

<400> SEQUENCE: 1

Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
            20                  25                  30

Gly Thr Phe Arg Leu Ile Gly Glu Lys Ser Leu Leu Cys Ile Thr Lys
            35                  40                  45

Asp Lys Val Asp Gly Thr Trp Asp Lys Pro Ala Pro Lys Cys Glu Tyr
            50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                85                  90                  95

Ala Cys Lys Thr Asn Phe Ser Met Asn Gly Asn Lys Ser Val Trp Cys
                100                 105                 110

-continued

```
Gln Ala Asn Asn Met Trp Gly Pro Thr Arg Leu Pro Thr Cys Val Ser
        115                 120                 125

Val Phe Pro Leu Glu Cys Pro Ala Leu Pro Met Ile His Asn Gly His
    130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
                165                 170                 175

Cys Leu Ser Ser Gly Lys Trp Ser Ala Val Pro Pro Thr Cys Glu Glu
                180                 185                 190

Ala Arg Cys Lys Ser Leu Gly Arg Phe Pro Asn Gly Lys Val Lys Glu
                195                 200                 205

Pro Pro Ile Leu Arg Val Gly Val Thr Ala Asn Phe Phe Cys Asp Glu
    210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Glu Glu Ile Phe Cys
                245                 250                 255

Pro Ser Pro Pro Pro Ile Leu Asn Gly Arg His Ile Gly Asn Ser Leu
                260                 265                 270

Ala Asn Val Ser Tyr Gly Ser Ile Val Thr Tyr Thr Cys Asp Pro Asp
                275                 280                 285

Pro Glu Glu Gly Val Asn Phe Ile Leu Ile Gly Glu Ser Thr Leu Arg
    290                 295                 300

Cys Thr Val Asp Ser Gln Lys Thr Gly Thr Trp Ser Gly Pro Ala Pro
305                 310                 315                 320

Arg Cys Glu Leu Ser Thr Ser Ala Val Gln Cys Pro His Pro Gln Ile
                325                 330                 335

Leu Arg Gly Arg Met Val Ser Gly Gln Lys Asp Arg Tyr Thr Tyr Asn
                340                 345                 350

Asp Thr Val Ile Phe Ala Cys Met Phe Gly Phe Thr Leu Lys Gly Ser
                355                 360                 365

Lys Gln Ile Arg Cys Asn Ala Gln Gly Thr Trp Glu Pro Ser Ala Pro
    370                 375                 380

Val Cys Glu Lys Glu Cys Gln Ala Pro Pro Asn Ile Leu Asn Gly Gln
385                 390                 395                 400

Lys Glu Asp Arg His Met Val Arg Phe Asp Pro Gly Thr Ser Ile Lys
                405                 410                 415

Tyr Ser Cys Asn Pro Gly Tyr Val Leu Val Gly Glu Glu Ser Ile Gln
                420                 425                 430

Cys Thr Ser Glu Gly Val Trp Thr Pro Pro Val Pro Gln Cys Lys Val
                435                 440                 445

Ala Ala Cys Glu Ala Thr Gly Arg Gln Leu Leu Thr Lys Pro Gln His
    450                 455                 460

Gln Phe Val Arg Pro Asp Val Asn Ser Ser Cys Gly Glu Gly Tyr Lys
465                 470                 475                 480

Leu Ser Gly Ser Val Tyr Gln Glu Cys Gln Gly Thr Ile Pro Trp Phe
                485                 490                 495

Met Glu Ile Arg Leu Cys Lys Glu Ile Thr Cys Pro Pro Pro Pro Val
                500                 505                 510

Ile Tyr Asn Gly Ala His Thr Gly Ser Ser Leu Glu Asp Phe Pro Tyr
                515                 520                 525

Gly Thr Thr Val Thr Tyr Thr Cys Asn Pro Gly Pro Glu Arg Gly Val
```

-continued

```
            530                 535                 540

Glu Phe Ser Leu Ile Gly Glu Ser Thr Ile Arg Cys Thr Ser Asn Asp
545                 550                 555                 560

Gln Glu Arg Gly Thr Trp Ser Gly Pro Ala Pro Leu Cys Lys Leu Ser
                565                 570                 575

Leu Leu Ala Val Gln Cys Ser His Val His Ile Ala Asn Gly Tyr Lys
                580                 585                 590

Ile Ser Gly Lys Glu Ala Pro Tyr Phe Tyr Asn Asp Thr Val Thr Phe
                595                 600                 605

Lys Cys Tyr Ser Gly Phe Thr Leu Lys Gly Ser Ser Gln Ile Arg Cys
        610                 615                 620

Lys Ala Asp Asn Thr Trp Asp Pro Glu Ile Pro Val Cys Glu Lys Glu
625                 630                 635                 640

Thr Cys Gln His Val Arg Gln Ser Leu Gln Glu Leu Pro Ala Gly Ser
                645                 650                 655

Arg Val Glu Leu Val Asn Thr Ser Cys Gln Asp Gly Tyr Gln Leu Thr
                660                 665                 670

Gly His Ala Tyr Gln Met Cys Gln Asp Ala Glu Asn Gly Ile Trp Phe
        675                 680                 685

Lys Lys Ile Pro Leu Cys Lys Val Ile His Cys His Pro Pro Pro Val
        690                 695                 700

Ile Val Asn Gly Lys His Thr Gly Met Met Ala Glu Asn Phe Leu Tyr
705                 710                 715                 720

Gly Asn Glu Val Ser Tyr Glu Cys Asp Gln Gly Phe Tyr Leu Leu Gly
                725                 730                 735

Glu Lys Lys Leu Gln Cys Arg Ser Asp Ser Lys Gly His Gly Ser Trp
                740                 745                 750

Ser Gly Pro Ser Pro Gln Cys Leu Arg Ser Pro Pro Val Thr Arg Cys
        755                 760                 765

Pro Asn Pro Glu Val Lys His Gly Tyr Lys Leu Asn Lys Thr His Ser
        770                 775                 780

Ala Tyr Ser His Asn Asp Ile Val Tyr Val Asp Cys Asn Pro Gly Phe
785                 790                 795                 800

Ile Met Asn Gly Ser Arg Val Ile Arg Cys His Thr Asp Asn Thr Trp
                805                 810                 815

Val Pro Gly Val Pro Thr Cys Ile Lys Lys Ala Phe Ile Gly Cys Pro
        820                 825                 830

Pro Pro Pro Lys Thr Pro Asn Gly Asn His Thr Gly Gly Asn Ile Ala
        835                 840                 845

Arg Phe Ser Pro Gly Met Ser Ile Leu Tyr Ser Cys Asp Gln Gly Tyr
        850                 855                 860

Leu Leu Val Gly Glu Ala Leu Leu Leu Cys Thr His Glu Gly Thr Trp
865                 870                 875                 880

Ser Gln Pro Ala Pro His Cys Lys Glu Val Asn Cys Ser Ser Pro Ala
                885                 890                 895

Asp Met Asp Gly Ile Gln Lys Gly Leu Glu Pro Arg Lys Met Tyr Gln
        900                 905                 910

Tyr Gly Ala Val Val Thr Leu Glu Cys Glu Asp Gly Tyr Met Leu Glu
        915                 920                 925

Gly Ser Pro Gln Ser Gln Cys Gln Ser Asp His Gln Trp Asn Pro Pro
        930                 935                 940

Leu Ala Val Cys Arg Ser Arg Ser Leu Ala Pro Val Leu Cys Gly Ile
945                 950                 955                 960
```

```
Ala Ala Gly Leu Ile Leu Leu Thr Phe Leu Ile Val Ile Thr Leu Tyr
                965                 970                 975

Val Ile Ser Lys His Arg Ala Arg Asn Tyr Tyr Thr Asp Thr Ser Gln
                980                 985                 990

Lys Glu Ala Phe His Leu Glu Ala  Arg Glu Val Tyr Ser  Val Asp Pro
            995             1000             1005

Tyr Asn  Pro Ala Ser
        1010

<210> SEQ ID NO 2
<211> LENGTH: 5
<212> TYPE: PRT
<213> ORGANISM: Human

<400> SEQUENCE: 2

Phe Asn Lys Tyr Ser
1               5

<210> SEQ ID NO 3
<211> LENGTH: 449
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 3

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
            20                  25                  30

Ser Tyr Tyr Trp Gly Trp Ile Arg Gln Pro Pro Gly Lys Gly Leu Glu
            35                  40                  45

Trp Ile Gly Ser Ile His Tyr Ser Gly Ser Thr Tyr Tyr Asn Pro Pro
        50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Gly Gly Pro Arg His Gly Trp Ser Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Ala Gly Ala Pro
225                 230                 235                 240
```

```
Ser Val Phe Leu Phe Pro Pro Lys Pro Lys Asp Thr Leu Met Ile Ser
                245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val Ser Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
        420             425             430

Ala Leu His Asn His Tyr Thr Gln Lys Ser Leu Ser Leu Ser Pro Gly
        435             440             445

Lys

<210> SEQ ID NO 4
<211> LENGTH: 214
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 4

Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Glu Tyr
            20              25              30

Leu Asn Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Tyr Cys Gln Gln Asp Ser Asn Leu Pro Ile
            85              90              95

Thr Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 5
<211> LENGTH: 119
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 5

Gln Leu Gln Leu Gln Glu Ser Gly Pro Gly Leu Val Lys Pro Ser Glu
1                   5                   10                  15

Thr Leu Ser Leu Thr Cys Thr Val Ser Gly Gly Ser Ile Ser Ser Asp
                20                  25                  30

Ser Tyr Tyr Trp Gly Trp Ile Arg Gln Pro Pro Gly Lys Gly Leu Glu
                35                  40                  45

Trp Ile Gly Ser Ile His Tyr Ser Gly Ser Thr Tyr Tyr Asn Pro Pro
        50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Gly Pro Arg His Gly Trp Ser Trp Gly Gln Gly
                100                 105                 110

Thr Leu Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 6

Asp Ile Gln Met Thr Gln Ser Pro Ser Ser Leu Ser Ala Ser Val Gly
1                   5                   10                  15

Asp Arg Val Thr Ile Thr Cys Gln Ala Ser Gln Asp Ile Ser Glu Tyr
                20                  25                  30

Leu Asn Trp Tyr Gln Gln Lys Pro Gly Lys Ala Pro Lys Leu Leu Ile
                35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Ser Asn Leu Pro Ile
                85                  90                  95

```
Thr Phe Gly Gly Gly Thr Lys Val Glu Ile Lys
            100                 105

<210> SEQ ID NO 7
<211> LENGTH: 7
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 7

Ser Asp Ser Tyr Tyr Trp Gly
1               5

<210> SEQ ID NO 8
<211> LENGTH: 16
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 8

Ser Ile His Tyr Ser Gly Ser Thr Tyr Tyr Asn Pro Pro Leu Glu Ser
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 9

Glu Gly Gly Pro Arg His Gly Trp Ser
1               5

<210> SEQ ID NO 10
<211> LENGTH: 11
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 10

Gln Ala Ser Gln Asp Ile Ser Glu Tyr Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 11

Asp Ala Ser Asn Leu Glu Thr
1               5

<210> SEQ ID NO 12
<211> LENGTH: 9
<212> TYPE: PRT
<213> ORGANISM: Artificial Sequence
```

-continued

```
<220> FEATURE:
<223> OTHER INFORMATION: Amino acid sequence identified using molecular
     biology techniques

<400> SEQUENCE: 12

Gln Gln Asp Ser Asn Leu Pro Ile Thr
1               5

<210> SEQ ID NO 13
<211> LENGTH: 1347
<212> TYPE: DNA
<213> ORGANISM: Artificial Sequence
<220> FEATURE:
<223> OTHER INFORMATION: Nucleic acid sequence identified using
     molecular biology techniques

<400> SEQUENCE: 13
cagctccagc tgcaggagag cggcccaggc ctggtgaaac ccagcgagac cctgagcctg        60
acctgcaccg tgagcggagg cagcatcagc tccgacagct actactgggg ctggattagg       120
cagcctcccg gcaagggcct ggagtggatc ggaagcatcc actacagcgg cagcaccctac      180 tacaacccac ccctggagag cagggtgacc atcagcgtgg acaccagcaa gaaccagttc       240
agcctgaagc tgagcagcgt cacagcagcc gacaccgccg tgtactattg cgccagggag       300
ggcggaccca ggcacggctg gagctggggc cagggcaccc tggtgaccgt gagcagcgca       360
agcaccaagg gccccagcgt gttccccctg gcccccagca gcaagagcac cagcggcggc       420
acagccgccc tgggctgcct ggtgaaggac tacttccccg agcccgtgac cgtgtcctgg       480
aacagcggag ccctgaccag cggcgtgcac accttccccg ccgtgctgca gagcagcggc       540
ctgtacagcc tgagcagcgt ggtgaccgtg cccagcagca gcctgggcac ccagacctac       600
atctgtaacg tgaaccacaa gcccagcaac accaaggtgg acaagaaggt ggagcccaag       660
agctgtgaca gacccacac ctgcccccccc tgccctgccc ccgagctggc cggagccccc       720
agcgtgttcc tgttcccccc caagcctaag gacaccctga tgatcagcag aaccccccgag       780 gtgacctgtg tggtggtgga tgtgagccac gaggaccctg aggtgaagtt caactggtac       840
gtggacggcg tggaggtgca caatgccaag accaagcccca gggaggagca gtacaacagc       900
acctaccggg tggtgtccgt gctgaccgtg ctgcaccagg attggctgaa cggcaaggag       960
tacaagtgta aggtgtccaa caaggcccct cctgccccta tcgagaaaac catcagcaag      1020
gccaagggcc agcccagaga gccccaggtg tacaccctgc cccctagcag agatgagctg      1080
accaagaacc aggtgtccct gacctgcctg gtgaagggct tctaccccag cgacatcgcc      1140
gtggagtggg agagcaacgg ccagcccgag aacaactaca agaccacccc ccctgtgctg      1200
gacagcgatg gcagcttctt cctgtacagc aagctgaccg tggacaagag cagatggcag      1260
cagggcaacg tgttcagctg ctccgtgatg cacgaggccc tgcacaatca ctacacccag      1320
aagagcctga gcctgtcccc tggcaag                                          1347

<210> SEQ ID NO 14
<211> LENGTH: 642
<212> TYPE: DNA
<213> ORGANISM: Artificial Sequence
<220> FEATURE:
<223> OTHER INFORMATION: Nucleic acid sequence identified using
     molecular biology techniques

<400> SEQUENCE: 14
gacatccaga tgactcagtc cccctctagc ctgagcgcta gcgtgggcga cagggtgacc        60
```

-continued

```
atcacctgcc aggccagcca ggacatcagc gagtacctga actggtacca gcagaagccc      120
ggcaaggccc ccaaactgct gatctacgac gcctcaaacc tcgagaccgg cgtgcctagc      180
aggtttagcg gcagcggcag cggcaccgac ttcaccttca ccatcagcag cctgcagccc      240
gaggatatcg ccacctacta ctgccagcag gacagcaacc tgcccatcac cttcggcgga      300
ggcaccaagg tggagattaa cgtacggtg gccgccccca gcgtgttcat cttcccccc      360 agcgatgagc agctgaagag cggcaccgcc agcgtggtgt gtctgctgaa caacttctac      420
ccccgggagg ccaaggtgca gtggaaggtg gacaatgccc tgcagagcgg caacagccag      480
gagagcgtga ccgagcagga cagcaaggac tccacctaca gcctgagcag caccctgacc      540
ctgagcaagg ccgactacga gaagcacaag gtgtacgcct gtgaggtgac ccaccagggc      600
ctgtccagcc ccgtgaccaa gagcttcaac cggggcgagt gc                        642
```

```
<210> SEQ ID NO 15
<211> LENGTH: 449
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 15

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile His Asn Ser Gly Ser Thr Tyr Tyr Asn Pro Pro
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Gly Pro Arg His Gly Trp Ser Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Ala Gly Ala Pro
225                 230                 235                 240

Ser Val Phe Leu Phe Pro Pro Lys Pro Lys Asp Thr Leu Met Ile Ser
                245                 250                 255
```

-continued

```
Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```

```
<210> SEQ ID NO 16
<211> LENGTH: 214
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 16

Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Thr Phe
            20              25              30

Leu Asn Trp Tyr Gln Gln Lys Pro Gly Lys Ala Pro Lys Leu Leu Ile
            35              40              45

Tyr Asp Ala Ser Asn Leu Glu Thr Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Tyr Cys Gln Gln Asp Ser Ile Leu Pro Ile
            85              90              95

Thr Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 119
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 17

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile His Asn Ser Gly Ser Thr Tyr Tyr Asn Pro Pro
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Gly Gly Pro Arg His Gly Trp Ser Trp Gly Gln Gly
            100                 105                 110

Thr Leu Val Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Thr Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Ser Ile Leu Pro Ile
            85                  90                  95

Thr Phe Gly Gly Gly Thr Lys Val Glu Ile Lys
        100                 105
```

-continued

<210> SEQ ID NO 19
<211> LENGTH: 7
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 19

Ser Ser Ser Tyr Tyr Trp Gly
1               5

<210> SEQ ID NO 20
<211> LENGTH: 16
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 20

Ser Ile His Asn Ser Gly Ser Thr Tyr Tyr Asn Pro Pro Leu Lys Ser
1               5                   10                  15

<210> SEQ ID NO 21
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 21

Glu Gly Gly Pro Arg His Gly Trp Ser
1               5

<210> SEQ ID NO 22
<211> LENGTH: 11
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 22

Gln Ala Ser Gln Asp Ile Ser Thr Phe Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 23

Asp Ala Ser Asn Leu Glu Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

```
<400> SEQUENCE: 24

Gln Gln Asp Ser Ile Leu Pro Ile Thr
1               5

<210> SEQ ID NO 25
<211> LENGTH: 1347
<212> TYPE: DNA
<213> ORGANISM: Artificial Sequence
<220> FEATURE:
<223> OTHER INFORMATION: Nucleic acid sequence identified using
      molecular biology techniques

<400> SEQUENCE: 25
cagctccagc tgcaggagag cggcccaggc ctggtgaaac ccagcgagac cctgagcctg      60
acctgcaccg tgagcggagg cagcatcagc tccagcagct actactgggg ctggattagg     120
cagcctcccg gcaagggcct ggagtggatc ggaagcatcc acaacagcgg cagcacctac     180
tacaacccac ccctgaagag cagggtgacc atcagcgtgg acaccagcaa gaaccagttc     240
agcctgaagc tgagcagcgt cacagcagcc gacaccgccg tgtactattg cgccagggag     300
ggcggaccca ggcacggctg gagctggggc cagggcaccc tggtgaccgt gagcagcgca     360
agcaccaagg gccccagcgt gttccccctg gcccccagca gcaagagcac cagcggcggc     420
acagccgccc tgggctgcct ggtgaaggac tacttccccg agcccgtgac cgtgtcctgg     480
aacagcggag ccctgaccag cggcgtgcac accttccccg ccgtgctgca gagcagcggc     540
ctgtacagcc tgagcagcgt ggtgaccgtg cccagcagca gcctgggcac ccagacctac     600
atctgtaacg tgaaccacaa gcccagcaac accaaggtgg acaagaaggt ggagcccaag     660
agctgtgaca gacccacac ctgcccccc tgccctgccc ccgagctggc cggagccccc     720
agcgtgttcc tgttcccccc caagcctaag gacaccctga tgatcagcag aaccccccgag     780 gtgacctgtg tggtggtgga tgtgagccac gaggaccctg aggtgaagtt caactggtac     840
gtggacggcg tggaggtgca caatgccaag accaagccca gggaggagca gtacaacagc     900
acctaccggg tggtgtccgt gctgaccgtg ctgcaccagg attggctgaa cggcaaggag     960
tacaagtgta aggtgtccaa caaggccctg cctgcccta tcgagaaaac catcagcaag    1020
gccaagggcc agcccagaga gccccaggtg tacaccctgc ccccctagcag agatgagctg    1080 accaagaacc aggtgtccct gacctgcctg gtgaagggct tctaccccag cgacatcgcc    1140
gtggagtggg agagcaacgg ccagcccgag aacaactaca gaccaccccc cctgtgctg     1200 gacagcgatg gcagcttctt cctgtacagc aagctgaccg tggacaagag cagatggcag    1260
cagggcaacg tgttcagctg ctccgtgatg cacgaggccc tgcacaatca ctacacccag    1320
aagagcctga gctgtcccc tggcaag                                          1347

<210> SEQ ID NO 26
<211> LENGTH: 642
<212> TYPE: DNA
<213> ORGANISM: Artificial Sequence
<220> FEATURE:
<223> OTHER INFORMATION: Nucleic acid sequence identified using
      molecular biology techniques

<400> SEQUENCE: 26
gacatccaga tgactcagtc cccctctagc ctgagcgcta gcgtgggcga cagggtgacc      60
atcacctgcc aggccagcca ggacatcagc accttcctga actggtacca gcagaagccc     120
ggcaaggccc ccaaactgct gatctacgac gcctcaaacc tcgagaccgg cgtgcctagc     180
```

-continued

```
aggtttagcg gcagcggcag cggcaccgac ttcaccttca ccatcagcag cctgcagccc        240
gaggatatcg ccacctacta ctgccagcag gacagcatcc tgcccatcac cttcggcgga        300
ggcaccaagg tggagattaa gcgtacggtg gccgccccca gcgtgttcat cttcccccc        360 agcgatgagc agctgaagag cggcaccgcc agcgtggtgt gtctgctgaa caacttctac        420
cccggggagg ccaaggtgca gtggaaggtg gacaatgccc tgcagagcgg caacagccag        480
gagagcgtga ccgagcagga cagcaaggac tccaccctaca gcctgagcag caccctgacc        540
ctgagcaagg ccgactacga gaagcacaag gtgtacgcct gtgaggtgac ccaccagggc        600
ctgtccagcc ccgtgaccaa gagcttcaac cggggcgagt gc                          642
```

```
<210> SEQ ID NO 27
<211> LENGTH: 449
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 27

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile His Tyr Ser Gly Ser Thr Tyr Tyr Asn Pro Pro
    50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Gly Gly Pro Arg His Gly Trp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

-continued

```
              275                 280                 285
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 28
<211> LENGTH: 214
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser His Asp Ile Ser Asn Phe
                20                  25                  30

Leu Asn Trp Tyr Gln Gln Lys Pro Gly Lys Ala Pro Lys Leu Leu Ile
            35                  40                  45

Tyr Asp Thr Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Ser Ile Leu Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
                 180             185             190
Ala Cys Glu Val Thr His Gln Gly Leu Ser Ser Pro Val Thr Lys Ser
         195             200             205

Phe Asn Arg Gly Glu Cys
    210

<210> SEQ ID NO 29
<211> LENGTH: 119
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 29

Gln Leu Gln Leu Gln Glu Ser Gly Pro Gly Leu Val Lys Pro Ser Glu
1               5               10              15

Thr Leu Ser Leu Thr Cys Thr Val Ser Gly Gly Ser Ile Ser Ser Ser
         20              25              30

Ser Tyr Tyr Trp Gly Trp Ile Arg Gln Pro Pro Gly Lys Gly Leu Glu
         35              40              45

Trp Ile Gly Ser Ile His Tyr Ser Gly Ser Thr Tyr Tyr Asn Pro Pro
    50              55              60

Leu Glu Ser Arg Val Thr Ile Ser Val Asp Thr Ser Lys Asn Gln Phe
65              70              75              80

Ser Leu Lys Leu Ser Ser Val Thr Ala Ala Asp Thr Ala Val Tyr Tyr
            85              90              95

Cys Ala Arg Glu Gly Gly Pro Arg His Gly Trp Ser Trp Gly Gln Gly
            100             105             110

Thr Leu Val Thr Val Ser Ser
        115

<210> SEQ ID NO 30
<211> LENGTH: 107
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 30

Asp Ile Gln Met Thr Gln Ser Pro Ser Ser Leu Ser Ala Ser Val Gly
1               5               10              15

Asp Arg Val Thr Ile Thr Cys Gln Ala Ser His Asp Ile Ser Asn Phe
         20              25              30

Leu Asn Trp Tyr Gln Gln Lys Pro Gly Lys Ala Pro Lys Leu Leu Ile
         35              40              45

Tyr Asp Thr Ser Asn Leu Glu Thr Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Tyr Cys Gln Gln Asp Ser Ile Leu Pro Ile
            85              90              95

Thr Phe Gly Gly Gly Thr Lys Val Glu Ile Lys
        100             105

<210> SEQ ID NO 31
<211> LENGTH: 7
<212> TYPE: PRT
```

-continued

```
<213> ORGANISM: Artificial Sequence
<220> FEATURE:
<223> OTHER INFORMATION: Amino acid sequence identified using molecular
      biology techniques

<400> SEQUENCE: 31

Ser Ser Ser Tyr Tyr Trp Gly
1               5

<210> SEQ ID NO 32
<211> LENGTH: 16
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 32

Ser Ile His Tyr Ser Gly Ser Thr Tyr Tyr Asn Pro Pro Leu Glu Ser
1               5                   10                  15

<210> SEQ ID NO 33
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 33

Glu Gly Gly Pro Arg His Gly Trp Ser
1               5

<210> SEQ ID NO 34
<211> LENGTH: 11
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 34

Gln Ala Ser His Asp Ile Ser Asn Phe Leu Asn
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 35

Asp Thr Ser Asn Leu Glu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 36

Gln Gln Asp Ser Ile Leu Pro Ile Thr
1               5
```

-continued

```
<210> SEQ ID NO 37
<211> LENGTH: 1347
<212> TYPE: DNA
<213> ORGANISM: Artificial Sequence
<220> FEATURE:
<223> OTHER INFORMATION: Nucleic acid sequence identified using
      molecular biology techniques

<400> SEQUENCE: 37
cagctccagc tgcaggagag cggcccaggc ctggtgaaac ccagcgagac cctgagcctg        60
acctgcaccg tgagcggagg cagcatcagc tccagcagct actactgggg ctggattagg       120
cagcctcccg gcaagggcct ggagtggatc ggaagcatcc actacagcgg cagcacctac       180
tacaacccac ccctggagag cagggtgacc atcagcgtgg acaccagcaa gaaccagttc       240
agcctgaagc tgagcagcgt cacagcagcc gacaccgccg tgtactattg cgccagggag       300
ggcggaccca ggcacggctg gagctggggc cagggcaccc tggtgaccgt gagcagcgca       360
agcaccaagg gccccagcgt gttccccctg gcccccagca gcaagagcac cagcggcggc       420
acagccgccc tgggctgcct ggtgaaggac tacttccccg agcccgtgac cgtgtcctgg       480
aacagcggag ccctgaccag cggcgtgcac accttccccg ccgtgctgca gagcagcggc       540
ctgtacagcc tgagcagcgt ggtgaccgtg cccagcagca gcctgggcac ccagacctac       600
atctgtaacg tgaaccacaa gcccagcaac accaaggtgg acaagaaggt ggagcccaag       660
agctgtgaca gacccacac ctgcccccccc tgccctgccc ccgagctggc cggagccccc       720
agcgtgttcc tgttcccccc caagcctaag gacaccctga tgatcagcag aaccccccgag       780 gtgacctgtg tggtggtgga tgtgagccac gaggaccctg aggtgaagtt caactggtac       840
gtggacggcg tggaggtgca caatgccaag accaagccca gggaggagca gtacaacagc       900
acctaccggg tggtgtccgt gctgaccgtg ctgcaccagg attggctgaa cggcaaggag       960
tacaagtgta aggtgtccaa caaggccctg cctgccccta tcgagaaaac catcagcaag      1020
gccaagggcc agcccagaga gccccaggtg tacaccctgc ccctagcag agatgagctg      1080 accaagaacc aggtgtccct gacctgcctg gtgaagggct tctaccccag cgacatcgcc      1140
gtggagtggg agagcaacgg ccagcccgag aacaactaca agaccacccc ccctgtgctg      1200
gacagcgatg gcagcttctt cctgtacagc aagctgaccg tggacaagag cagatggcag      1260
cagggcaacg tgttcagctg ctccgtgatg cacgaggccc tgcacaatca ctacacccag      1320
aagagcctga gcctgtcccc ctggcaag                                        1347

<210> SEQ ID NO 38
<211> LENGTH: 642
<212> TYPE: DNA
<213> ORGANISM: Artificial Sequence
<220> FEATURE:
<223> OTHER INFORMATION: Nucleic acid sequence identified using
      molecular biology techniques

<400> SEQUENCE: 38
gacatccaga tgactcagtc cccctctagc ctgagcgcta gcgtgggcga cagggtgacc        60
atcacctgcc aggccagcca cgacatcagc aacttcctga actggtacca gcagaagccc       120
ggcaaggccc ccaaactgct gatctacgac acctcaaacc tcgagaccgg cgtgcctagc       180
aggtttagcg gcagcggcag cggcaccgac ttcaccttca ccatcagcag cctgcagccc       240
gaggatatcg ccacctacta ctgccagcag gacagcatcc tgcccatcac cttcggcgga       300
```

```
ggcaccaagg tggagattaa gcgtacggtg gccgccccca gcgtgttcat cttcccccc      360 agcgatgagc agctgaagag cggcaccgcc agcgtggtgt gtctgctgaa caacttctac      420
ccccgggagg ccaaggtgca gtggaaggtg gacaatgccc tgcagagcgg caacagccag      480
gagagcgtga ccgagcagga cagcaaggac tccacctaca gcctgagcag caccctgacc      540
ctgagcaagg ccgactacga gaagcacaag gtgtacgcct gtgaggtgac ccaccagggc      600
ctgtccagcc ccgtgaccaa gagcttcaac cggggcgagt gc                        642
```

```
<210> SEQ ID NO 39
<211> LENGTH: 11
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 39

Met Ile Ser Cys Gly Ser Pro Pro Pro Ile Leu
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 40

Met Ile Ser Cys Gly Ser Pro Pro Pro Ile Leu Asn Gly Arg Ile Ser
1               5                   10                  15

Tyr

<210> SEQ ID NO 41
<211> LENGTH: 8
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 41

Tyr Ser Thr Pro Ile Ala Val Gly
1               5

<210> SEQ ID NO 42
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 42

Tyr Ser Thr Pro Ile Ala Val Gly Thr
1               5

<210> SEQ ID NO 43
<211> LENGTH: 18
<212> TYPE: PRT
<213> ORGANISM: Artificial Sequence
<220> FEATURE:
<223> OTHER INFORMATION: Amino acid sequence identified using molecular
      biology techniques
```

<400> SEQUENCE: 43

Tyr Ser Thr Pro Ile Ala Val Gly Thr Val Ile Arg Tyr Ser Cys Ser
1               5                   10                  15

Gly Thr

<210> SEQ ID NO 44
<211> LENGTH: 10
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 44

Thr Val Ile Arg Tyr Ser Cys Ser Gly Thr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 45

Thr Val Ile Arg Tyr Ser Cys Ser Gly Thr Phe
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 46

Val Ile Arg Tyr Ser Cys Ser Gly Thr
1               5

<210> SEQ ID NO 47
<211> LENGTH: 8
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 47

Phe Arg Leu Ile Gly Glu Lys Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 48

Phe Arg Leu Ile Gly Glu Lys Ser Leu
1               5

<210> SEQ ID NO 49

```
<211> LENGTH: 10
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 49

Phe Arg Leu Ile Gly Glu Lys Ser Leu Leu
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 50

Arg Leu Ile Gly Glu Lys Ser Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 51

Arg Leu Ile Gly Glu Lys Ser Leu Leu
1               5

<210> SEQ ID NO 52
<211> LENGTH: 7
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 52

Ile Gly Glu Lys Ser Leu Leu
1               5

<210> SEQ ID NO 53
<211> LENGTH: 21
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 53

Gly Glu Lys Ser Leu Leu Cys Ile Thr Lys Asp Lys Val Asp Gly Thr
1               5                   10                  15

Trp Asp Lys Pro Ala
            20

<210> SEQ ID NO 54
<211> LENGTH: 10
<212> TYPE: PRT
<213> ORGANISM: Artificial Sequence
<220> FEATURE:
<223> OTHER INFORMATION: Amino acid sequence identified using molecular
      biology techniques
```

```
<400> SEQUENCE: 54

Cys Ile Thr Lys Asp Lys Val Asp Gly Thr
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 55

Cys Ile Thr Lys Asp Lys Val Asp Gly Thr Trp Asp Lys Pro Ala Pro
1               5                   10                  15

Lys Cys Glu Tyr
            20

<210> SEQ ID NO 56
<211> LENGTH: 15
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 56

Lys Val Asp Gly Thr Trp Asp Lys Pro Ala Pro Lys Cys Glu Tyr
1               5                   10                  15

<210> SEQ ID NO 57
<211> LENGTH: 10
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 57

Trp Asp Lys Pro Ala Pro Lys Cys Glu Tyr
1               5                   10

<210> SEQ ID NO 58
<211> LENGTH: 31
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 58

Phe Asn Lys Tyr Ser Ser Cys Pro Glu Pro Ile Val Pro Gly Gly Tyr
1               5                   10                  15

Lys Ile Arg Gly Ser Thr Pro Tyr Arg His Gly Asp Ser Val Thr
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 59
```

```
Phe Asn Lys Tyr Ser Ser Cys Pro Glu Pro Ile Val Pro Gly Gly Tyr
1               5                   10                  15

Lys Ile Arg Gly Ser Thr Pro Tyr Arg His Gly Asp Ser Val Thr Phe
            20                  25                  30

<210> SEQ ID NO 60
<211> LENGTH: 27
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 60

Ser Ser Cys Pro Glu Pro Ile Val Pro Gly Gly Tyr Lys Ile Arg Gly
1               5                   10                  15

Ser Thr Pro Tyr Arg His Gly Asp Ser Val Thr
            20                  25

<210> SEQ ID NO 61
<211> LENGTH: 16
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 61

Tyr Lys Ile Arg Gly Ser Thr Pro Tyr Arg His Gly Asp Ser Val Thr
1               5                   10                  15

<210> SEQ ID NO 62
<211> LENGTH: 17
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 62

Tyr Lys Ile Arg Gly Ser Thr Pro Tyr Arg His Gly Asp Ser Val Thr
1               5                   10                  15

Phe

<210> SEQ ID NO 63
<211> LENGTH: 15
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 63

Lys Ile Arg Gly Ser Thr Pro Tyr Arg His Gly Asp Ser Val Thr
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 64

Lys Ile Arg Gly Ser Thr Pro Tyr Arg His Gly Asp Ser Val Thr Phe
```

-continued

```
1               5               10              15

<210> SEQ ID NO 65
<211> LENGTH: 7
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 65

Phe Ala Cys Lys Thr Asn Phe
1               5

<210> SEQ ID NO 66
<211> LENGTH: 9
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 66

Ser Met Asn Gly Asn Lys Ser Val Trp
1               5

<210> SEQ ID NO 67
<211> LENGTH: 10
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 67

Ser Met Asn Gly Asn Lys Ser Val Trp Cys
1               5               10

<210> SEQ ID NO 68
<211> LENGTH: 12
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 68

Ser Met Asn Gly Asn Lys Ser Val Trp Cys Gln Ala
1               5               10

<210> SEQ ID NO 69
<211> LENGTH: 15
<212> TYPE: PRT
<213> ORGANISM: Artificial Sequence
<220> FEATURE:
<223> OTHER INFORMATION: Amino acid sequence identified using molecular
      biology techniques

<400> SEQUENCE: 69

Ser Met Asn Gly Asn Lys Ser Val Trp Cys Gln Ala Asn Asn Met
1               5               10              15

<210> SEQ ID NO 70
<211> LENGTH: 21
<212> TYPE: PRT
<213> ORGANISM: Artificial Sequence
<220> FEATURE:
<223> OTHER INFORMATION: Amino acid sequence identified using molecular
```

-continued

```
        biology techniques

<400> SEQUENCE: 70

Ser Met Asn Gly Asn Lys Ser Val Trp Cys Gln Ala Asn Asn Met Trp
1               5                   10                  15

Gly Pro Thr Arg Leu
            20

<210> SEQ ID NO 71
<211> LENGTH: 24
<212> TYPE: PRT
<213> ORGANISM: Artificial Sequence
<220> FEATURE:
<223> OTHER INFORMATION: Amino acid sequence identified using molecular
        biology techniques

<400> SEQUENCE: 71

Ser Met Asn Gly Asn Lys Ser Val Trp Cys Gln Ala Asn Asn Met Trp
1               5                   10                  15

Gly Pro Thr Arg Leu Pro Thr Cys
            20

<210> SEQ ID NO 72
<211> LENGTH: 9
<212> TYPE: PRT
<213> ORGANISM: Artificial Sequence
<220> FEATURE:
<223> OTHER INFORMATION: Amino acid sequence identified using molecular
        biology techniques

<400> SEQUENCE: 72

Asn Asn Met Trp Gly Pro Thr Arg Leu
1               5

<210> SEQ ID NO 73
<211> LENGTH: 13
<212> TYPE: PRT
<213> ORGANISM: Artificial Sequence
<220> FEATURE:
<223> OTHER INFORMATION: Amino acid sequence identified using molecular
        biology techniques

<400> SEQUENCE: 73

Asn Asn Met Trp Gly Pro Thr Arg Leu Pro Thr Cys Val
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Amino acid sequence identified using molecular
        biology techniques

<400> SEQUENCE: 74

Val Ser Val Phe Pro Leu Glu
1               5
```

The invention claimed is:

1. A complement receptor 2 (CR2) binding protein which binds to human CR2, wherein said CR2 binding protein binds to one or more residues within the linker between the two short complement repeat domains and/or near the C-terminus of human CR2, wherein said CR2 binding protein comprises in its heavy chain variable region a CDR1 comprising the amino acid sequence set out in SEQ ID NO:7, a CDR2 comprising the amino acid sequence set out in SEQ ID NO:8 and a CDR3 comprising the amino acid sequence set out in SEQ ID NO:9, and wherein said CR2 binding protein comprises in its light chain variable region a CDR1 comprising the amino acid sequence set out in SEQ ID NO:10, a CDR2 comprising the amino acid sequence set out in SEQ ID NO: 11 and a CDR3 comprising the amino acid sequence set out in SEQ ID NO:12.

2. The CR2 binding protein according to claim 1 wherein said CR2 binding protein comprises a variable light chain amino acid sequence as set out in SEQ ID NO: 6 and a variable heavy chain amino acid sequence as set out in SEQ ID NO:5.

3. The CR2 binding protein according to claim 2, wherein said CR2 binding protein comprises a light chain amino acid sequence as set out in SEQ ID NO:4 and a heavy chain amino acid sequence as set out in SEQ ID NO:3.

4. A pharmaceutical composition comprising a CR2 binding protein according to claim 1 and a pharmaceutically acceptable carrier or excipient.

5. An antibody which binds to human CR2, wherein said antibody comprises in its light chain variable region a CDR1 comprising the amino acid sequence set out in SEQ ID NO:10, a CDR2 comprising the amino acid sequence set out in SEQ ID NO:11 and a CDR3 comprising the amino acid sequence set out in SEQ ID NO: 12 and in its heavy chain variable region a CDR1 comprising the amino acid sequence set out in SEQ ID NO:7, a CDR2 comprising the amino acid sequence set out in SEQ ID NO:8 and a CDR3 comprising the amino acid sequence set out in SEQ ID NO:9.

6. The antibody according to claim 5 wherein said antibody comprises a variable light chain amino acid sequence as set out in SEQ ID NO:6 and wherein said antibody comprises a variable heavy chain amino acid sequence as set out in SEQ ID NO:5.

7. The antibody according claim 5 wherein said antibody comprises a light chain amino acid sequence as set out in SEQ ID NO:4 and wherein said antibody comprises a heavy chain amino acid sequence as set out in SEQ ID NO: 3.

8. A pharmaceutical composition comprising an antibody according to claim 5 and a pharmaceutically acceptable carrier or excipient.

* * * * *